(12) United States Patent
Py et al.

(10) Patent No.: US 8,007,193 B2
(45) Date of Patent: Aug. 30, 2011

(54) LATERALLY-ACTUATED DISPENSER WITH ONE-WAY VALVE FOR STORING AND DISPENSING SUBSTANCES

(75) Inventors: Daniel Py, Larchmont, NY (US); Julian Chan, Spring Valley, NY (US); David Fellows, Pound Ridge, NY (US); Eric E. Hartman, Ridgefield, CT (US); Bing He, Ridgewood, NY (US)

(73) Assignee: Medical Instill Technologies, Inc., New Milford, CT (US)

( * ) Notice: Subject to any disclaimer, the term of this patent is extended or adjusted under 35 U.S.C. 154(b) by 0 days.

(21) Appl. No.: 12/710,516

(22) Filed: Feb. 23, 2010

(65) Prior Publication Data

US 2010/0178097 A1    Jul. 15, 2010

Related U.S. Application Data

(63) Continuation of application No. 11/237,599, filed on Sep. 27, 2005, now Pat. No. 7,665,923.

(60) Provisional application No. 60/613,583, filed on Sep. 27, 2004, provisional application No. 60/699,607, filed on Jul. 15, 2005.

(51) Int. Cl.
  *A46B 11/02*    (2006.01)

(52) U.S. Cl. ........ 401/188 R; 401/11; 401/176; 401/265

(58) Field of Classification Search ................... 401/152, 401/153, 155, 156, 176, 179, 186, 188 R, 401/263, 265, 266, 11; 222/386.5, 387
See application file for complete search history.

(56) References Cited

U.S. PATENT DOCUMENTS

| | | | |
|---|---|---|---|
| 2,252,542 | A | 8/1941 | Beeh |
| 2,275,595 | A | 3/1942 | Schwartz |
| 2,388,321 | A | 11/1945 | Gereke |
| 2,442,503 | A | 6/1948 | Melnikoff |
| 2,642,607 | A | 6/1953 | Bozzalla |
| 2,715,236 | A | 8/1955 | Tereno |
| 2,725,595 | A | 12/1955 | Sisk et al. |

(Continued)

FOREIGN PATENT DOCUMENTS

DE    197 27 485 A1    1/1999

(Continued)

OTHER PUBLICATIONS

International Search Report for International Application No. PCT/US2005/035107, mailed Oct. 23, 2006.

(Continued)

*Primary Examiner* — David J Walczak
(74) *Attorney, Agent, or Firm* — McCarter & English, LLP

(57) ABSTRACT

A dispenser for dispensing a substance, such as a pharmaceutical, ophthalmic, dermatological, cosmeceutical, cosmetic or other product, has a body with a variable-volume storage chamber for storing the product. A dispensing portion of the dispenser is connected with the body and has a compression chamber in fluid communication with the storage chamber for receiving substance therefrom, and an outlet aperture coupled in fluid communication with the compression chamber. A one-way valve of the dispenser includes an axially-extending valve seat and an axially-extending flexible valve cover seated on the valve seat and defining a normally-closed, axially-extending seam therebetween forming a fluid-tight seal between the valve cover and valve seat. The flexible valve cover is movable relative to the valve seat and the seam is connectable in fluid communication with the outlet aperture to allow the passage of substance through the seam and out of the dispenser.

23 Claims, 18 Drawing Sheets

U.S. PATENT DOCUMENTS

| | | |
|---|---|---|
| 2,732,736 A | 1/1956 | Bonnie |
| 2,743,042 A | 4/1956 | Burgin |
| 3,160,329 A | 12/1964 | Radic et al. |
| 3,820,689 A | 6/1974 | Cocita |
| 3,864,047 A | 2/1975 | Sherrod |
| 4,002,182 A | 1/1977 | Michel |
| 4,301,948 A | 11/1981 | Czech et al. |
| 4,511,068 A | 4/1985 | Bossina |
| 4,564,130 A | 1/1986 | Eulenburg |
| 4,629,097 A | 12/1986 | Moore |
| 4,874,117 A | 10/1989 | Kay et al. |
| 4,981,479 A | 1/1991 | Py |
| 5,207,659 A | 5/1993 | Pennaneac'h et al. |
| 5,267,673 A | 12/1993 | Crosnier et al. |
| 5,267,986 A | 12/1993 | Py |
| 5,320,845 A | 6/1994 | Py |
| 5,401,259 A | 3/1995 | Py |
| 5,492,252 A | 2/1996 | Gueret |
| D368,774 S | 4/1996 | Py |
| 5,505,341 A | 4/1996 | Gueret |
| D374,719 S | 10/1996 | Py |
| 5,613,517 A | 3/1997 | Handler |
| 5,613,957 A | 3/1997 | Py |
| 5,641,004 A | 6/1997 | Py |
| 5,685,869 A | 11/1997 | Py |
| 5,687,884 A | 11/1997 | Bodin et al. |
| 5,738,067 A | 4/1998 | Landwehr et al. |
| 5,746,728 A | 5/1998 | Py |
| 5,769,585 A | 6/1998 | Podolsky |
| 5,772,347 A | 6/1998 | Gueret |
| 5,816,772 A | 10/1998 | Py |
| 5,855,322 A | 1/1999 | Py |
| 5,875,931 A | 3/1999 | Py |
| 5,879,095 A | 3/1999 | Gueret |
| 5,944,702 A | 8/1999 | Py |
| 6,010,036 A | 1/2000 | Bougamont et al. |
| 6,033,384 A | 3/2000 | Py |
| 6,053,433 A | 4/2000 | Py |
| 6,073,813 A | 6/2000 | Tanner |
| RE37,047 E | 2/2001 | Py |
| 6,254,579 B1 | 7/2001 | Cogger et al. |
| 6,382,472 B1 | 5/2002 | Shoval |
| 6,409,406 B1 | 6/2002 | Schwartzman |
| 6,471,095 B1 | 10/2002 | Cann |
| 6,604,561 B2 | 8/2003 | Py |
| 6,688,317 B2 | 2/2004 | Gueret |
| 6,708,846 B1 | 3/2004 | Fuchs et al. |
| 6,745,781 B2 | 6/2004 | Gueret |
| 6,761,286 B2 | 7/2004 | Py et al. |
| 7,000,806 B2 | 2/2006 | Py et al. |
| 7,226,231 B2 | 6/2007 | Py et al. |
| 7,278,553 B2 | 10/2007 | Py et al. |
| 7,322,491 B2 | 1/2008 | Py et al. |
| 7,347,389 B2 | 3/2008 | Ohnmacht et al. |
| 2002/0017294 A1 | 2/2002 | Py |
| 2002/0074362 A1 | 6/2002 | Py et al. |
| 2003/0089743 A1 | 5/2003 | Py et al. |
| 2004/0112925 A1 | 6/2004 | Py et al. |
| 2004/0161292 A1 | 8/2004 | Breidenbach et al. |
| 2005/0089358 A1 | 4/2005 | Py et al. |
| 2005/0165368 A1 | 7/2005 | Py et al. |
| 2005/0263543 A1 | 12/2005 | Py et al. |
| 2006/0065677 A1 | 3/2006 | Py et al. |
| 2006/0231519 A1 | 10/2006 | Py et al. |
| 2006/0237335 A1 | 10/2006 | Py et al. |

FOREIGN PATENT DOCUMENTS

| | | |
|---|---|---|
| JP | H6-2601 Y2 | 1/1994 |
| WO | WO 2004/062422 A | 7/2004 |

OTHER PUBLICATIONS

International Preliminary Report on Patentability for International Application No. PCT/US2005/035107, mailed Mar. 27, 2007.

Supplementary European Search Report, European Application No. EP 05 80 2158, mailed Jun. 10, 2008.

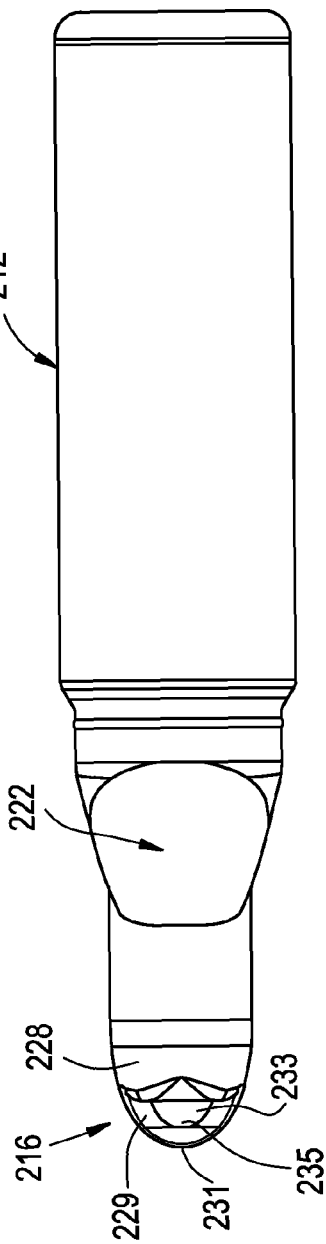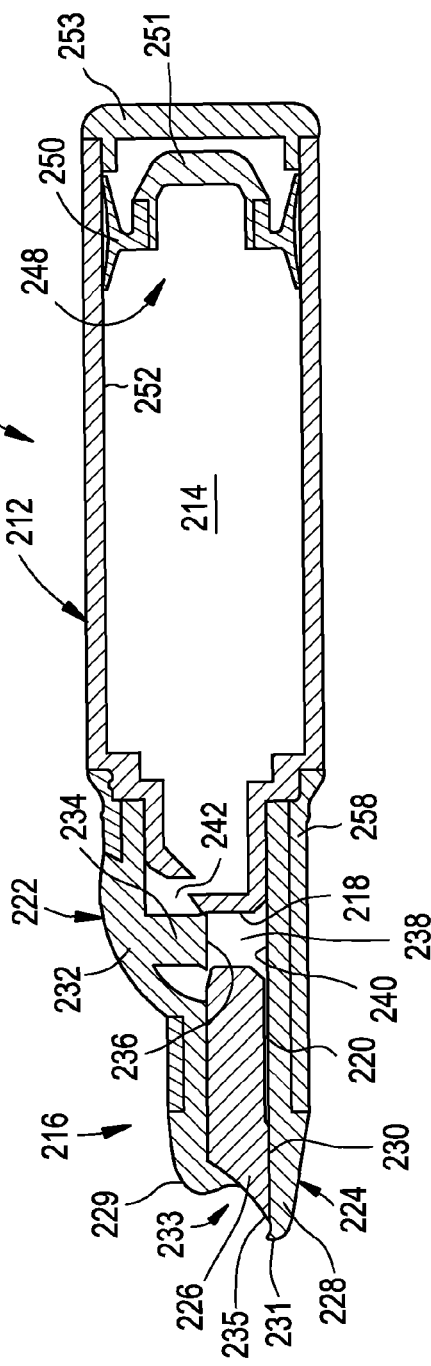

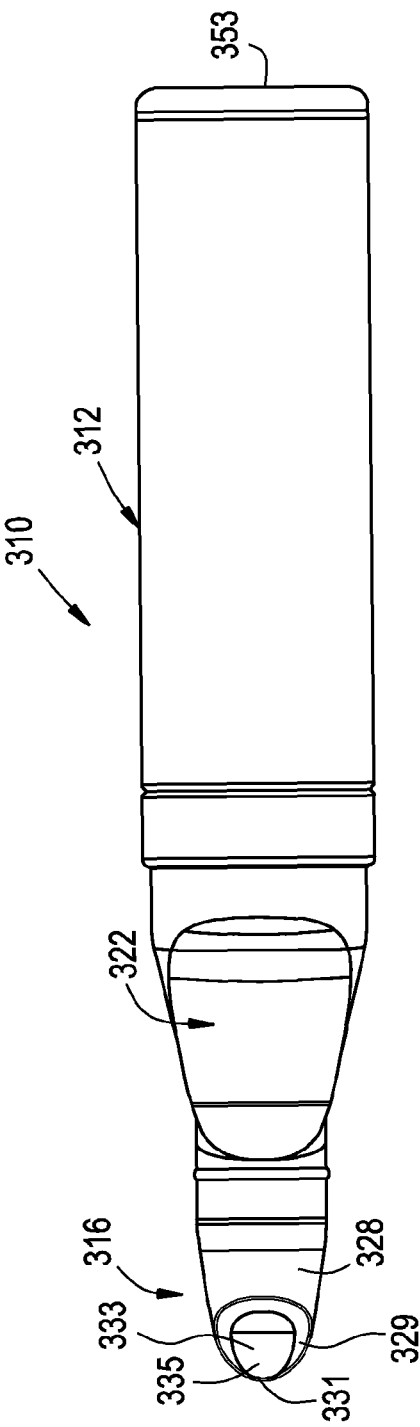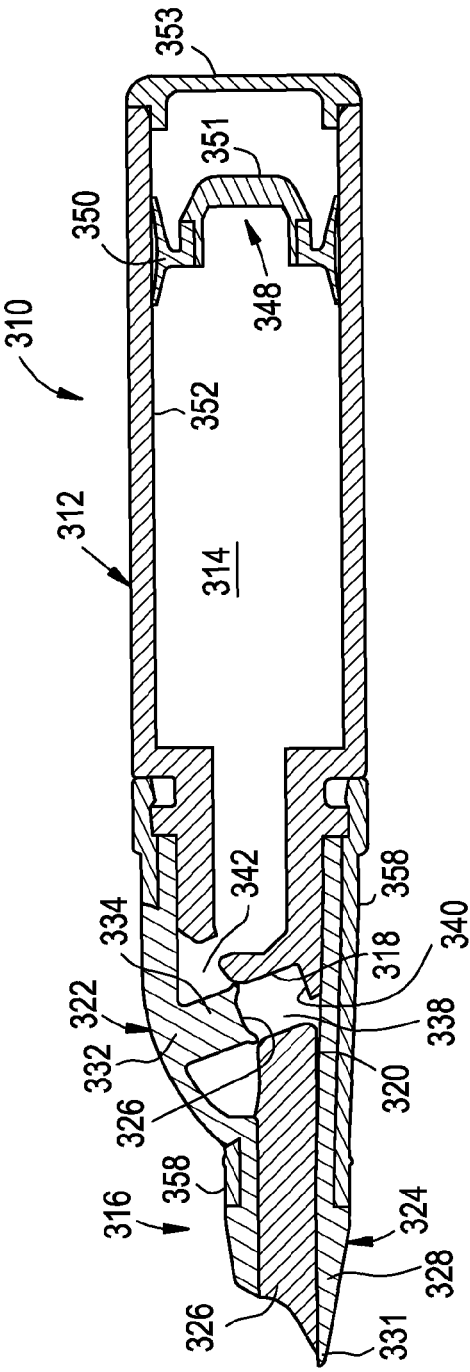

FIG. 17
FIG. 18
FIG. 19 ulation No. 60/613,583, filed Sep. 27, 2004, titled "Laterally-Actuated Dispenser with One-Way Valve for Storing and Dispensing Metered Amounts of Substances" and U.S. Provisional Application No. 60/699,607 filed Jul. 15, 2005 titled "Laterally-Actuated Dispenser with One-Way Valve for Storing and Dispensing Metered Amounts of Substances," each of which is hereby expressly incorporated by reference in its entirety as part of the present disclosure as if fully set forth herein. This patent application also contains subject matter similar to that disclosed in the commonly assigned U.S. Design patent application No. 29/214,062, filed on Sep. 27, 2004 titled "Dispenser with Laterally-Actuated Dispensing Valve," now patent No. D543,469 issued May 27, 2007, which is hereby expressly incorporated by reference as part of the present disclosure.

US 8,007,193 B2

LATERALLY-ACTUATED DISPENSER WITH ONE-WAY VALVE FOR STORING AND DISPENSING SUBSTANCES

CROSS-REFERENCE TO RELATED APPLICATION

This application is a continuation of U.S. application Ser. No. 11/237,599 filed Sep. 27, 2005, titled "Laterally-Actuated Dispenser with One-Way Valve for Storing and Dispensing Metered Amounts of Substances," now U.S. Pat. No. 7,665,923 issued Feb. 23, 2010, and claiming priority to U.S. Provisional Application No. 60/613,583, filed Sep. 27, 2004, titled "Laterally-Actuated Dispenser with One-Way Valve for Storing and Dispensing Metered Amounts of Substances" and U.S. Provisional Application No. 60/699,607 filed Jul. 15, 2005 titled "Laterally-Actuated Dispenser with One-Way Valve for Storing and Dispensing Metered Amounts of Substances," each of which is hereby expressly incorporated by reference in its entirety as part of the present disclosure as if fully set forth herein. This patent application also contains subject matter similar to that disclosed in the commonly assigned U.S. Design patent application No. 29/214,062, filed on Sep. 27, 2004 titled "Dispenser with Laterally-Actuated Dispensing Valve," now patent No. D543,469 issued May 27, 2007, which is hereby expressly incorporated by reference as part of the present disclosure.

FIELD OF THE INVENTION

The present invention relates to dispensers for containing and dispensing fluids and other substances, such as pharmaceutical, cosmeceutical, and cosmetic products, and more particularly, to dispensers for holding multiple doses of such fluids and other substances, and that include one-way valves for hermetically sealing the substances within the dispensers, and actuators for actuating pumps within the dispensers and dispensing metered doses of substances through the one-way valves.

BACKGROUND INFORMATION

Prior art dispensers for storing and dispensing multiple doses of substances, such as cosmetic dispensers for dispensing, for example, liquid lipstick or eye shadow, ophthalmic dispensers for dispensing ophthalmic products, such as eye drops, and pharmaceutical dispensers for dispensing pharmaceutical products, typically do not store the product, which may take the form of a liquid, cream, gel, suspension or other format, in a hermetically sealed storage chamber. In addition, such dispensers may be exposed to, and/or are applied to a user's facial or other body surfaces that may contain dirt, germs, bacteria or other unwanted contaminants. Such contaminants can penetrate through the dispensing openings in the dispensers and, in turn, contaminate the bulk of the products stored within the dispensers. As a result, the contaminants can be passed from one user to another or otherwise cause unhealthy conditions with further usage of the dispensers. Further, because the products stored within the dispensers are exposed to air, the products can degrade or spoil, and/or require preservatives to prevent such degradation and/or spoilage from occurring. In some circumstances, preservatives can cause allergic and/or other undesirable or negative reactions, such as unwanted dermatological reactions, or irritation of the eyes, skin or other tissues.

In other known prior art dispensers including storage chambers for storing multiple doses of substances, pumps for pumping the substances, and one-way valves for dispensing the pumped substances, there are multiple pieces required to form these parts and perform their functions. Such multiple parts can lead to manufacturing complexities and undesirable expense.

It is an object of the present invention to overcome one or more of the above-described drawbacks and/or disadvantages of the prior art.

SUMMARY OF THE INVENTION

The present invention is directed to a dispenser for dispensing a substance. In some embodiments, the dispenser comprises a body defining a variable-volume storage chamber for storing the substance, and a dispensing portion connected with the body. In certain embodiments, the dispensing portion defines a bore coupled in fluid communication with the storage chamber for receiving substance therefrom, and an outlet aperture coupled in fluid communication with the bore. A one-way valve of the dispenser includes an axially-extending valve seat and an axially-extending flexible valve cover seated on the valve seat and defining a normally-closed, axially-extending seam therebetween forming a fluid-tight seal between the valve cover and valve seat. The flexible valve cover is movable relative to the valve seat, and the seam is connectable in fluid communication with the outlet aperture to allow the passage of substance through the seam and out of the dispenser. The dispenser further comprises an actuator and piston assembly including a piston receivable within the bore, a manually-engageable actuator connected to the piston for moving the piston between first and second positions relative to the bore to dispense substance within the bore through the outlet aperture, and a spring coupled to at least one of the piston and the actuator for biasing the piston in a direction from one of the first and second positions toward the other.

Preferably, the actuator is located laterally with respect to the one-way valve. In one such embodiment, the piston defines a drive axis extending between the first and second positions, and the piston drive axis is oriented transverse to an axis of the valve. In one embodiment of the present invention, the piston drive axis is oriented at an angle of about 90° relative to the one-way valve axis. In another such embodiment, the piston drive axis is oriented at an acute angle relative to the one-way valve axis.

In the currently preferred embodiments of the present invention, the spring is approximately dome shaped. Also in some embodiments, the spring, piston and valve cover are formed integral with each other. In one such embodiment, the spring, piston and valve cover are molded in one piece.

In some embodiments of the present invention, the actuator and piston assembly defines a needle penetrable and resealable portion that permits the variable-volume storage chamber to be needle filled with a substance therethrough, and that allows the resulting needle hole to be thermally resealed, such as by application of laser energy thereto. In other embodiments of the present invention, a plunger is slidably received within the body of the dispenser and forms the variable-volume storage chamber, and includes a needle penetrable and resealable stopper or like portion that permits the variable-volume storage chamber to be needle filled with a substance therethrough, and that allows the resulting needle hole to be thermally resealed, such as by application of laser energy thereto.

In other embodiments of the invention, a first means forms the variable-volume chamber for storing the substance, and second means is coupled in fluid communication with the first means for dispensing metered dosages of substance, which third means for receiving a portion of the substance stored in the first means. Fourth means forms an external portion of the dispenser and is coupled in fluid communication with the second means (i) for normally sealing the second means along an annular, axially-extending seam and preventing the dispensing of substance below a threshold pressure through the second means, and (ii) for substantially sequentially opening the seam in an axial direction thereof to allow the passage of substance at a pressure greater than the threshold pressure through the second means and out of the dispenser. Fifth means is manually engageable and laterally depressible between first and second positions relative to an elongated axis of the dispenser for pressurizing the substance in the third means, which is connectible in fluid communication between the first means and the fourth means. During movement of the fifth means in the direction from the second position toward the first position, the first means is in fluid communication with the third means, and substance can flow from the first means into the third means. During movement of the fifth means in the direction from the first position toward the second position, the third means is not in fluid communication with the first means and a portion of the fifth means extends into the third means, which pressurizes substance within the third means above an opening pressure of the fourth means and, in turn, dispensing the substance through the fourth means and out of the dispenser.

In further embodiments, the dispensing portion defines a compression chamber coupled in fluid communication with the storage chamber to receive substance therefrom, and an outlet aperture is coupled in fluid communication with the compression chamber. The dispensing portion has a manually-engageable actuator mounted on it, which has a manually engageable surface on an external side of the actuator and a compression surface on an internal side of the actuator. The manually engageable surface is manually depressible between first and second positions to actuate the dispenser and allow the passage of substance through the one-way valve, as discussed above, and is normally biased in the direction from the second position toward the first position.

One advantage of the present invention is that the dispenser can store multiple doses of substances, such as pharmaceutical, cosmeceutical, cosmetic, or ophthalmic products, in a hermetically sealed, sterile condition throughout the shelf life and usage of the dispenser. Further, currently preferred embodiments of the dispenser can provide metered doses of the substance with a simple, one-handed actuation motion. Yet another advantage of the currently preferred embodiments of the present invention is that the valve cover and the actuator and piston assembly can be molded in one piece, and the body, dispensing portion and valve seat likewise can be molded in one piece, thus permitting a significantly reduced number of parts in comparison to prior art dispensers, and thereby reducing the complexity and manufacturing expense in comparison to such dispensers. A still further advantage of the present invention is that the actuator and piston assembly, or the plunger or other component forming the variable-volume storage chamber, can define a needle penetrable and thermally resealable portion, thereby permitting the dispenser to be needle filled and laser resealed.

Other objects and advantages of the present invention, and/or of the currently preferred embodiments thereof, will become apparent in view of the following detailed description of the currently preferred embodiments and the accompanying drawings.

BRIEF DESCRIPTION OF THE DRAWINGS

FIG. 8 is a top view of a third embodiment of a dispenser.

FIG. 9 is a cross-sectional view of the dispenser of FIG. 8.

FIG. 10 is a top view of a fourth embodiment of a dispenser.

FIG. 11 is a cross-sectional view of the dispenser of FIG. 10.

FIG. 17 is a cross-sectional view of a ninth embodiment of a dispenser.

FIG. 18 is a cross-sectional view of tenth embodiment of a dispenser.

FIG. 19 is a cross-sectional view of an eleventh embodiment of a dispenser.

DETAILED DESCRIPTION OF EMBODIMENTS OF THE INVENTION

Figure 1:
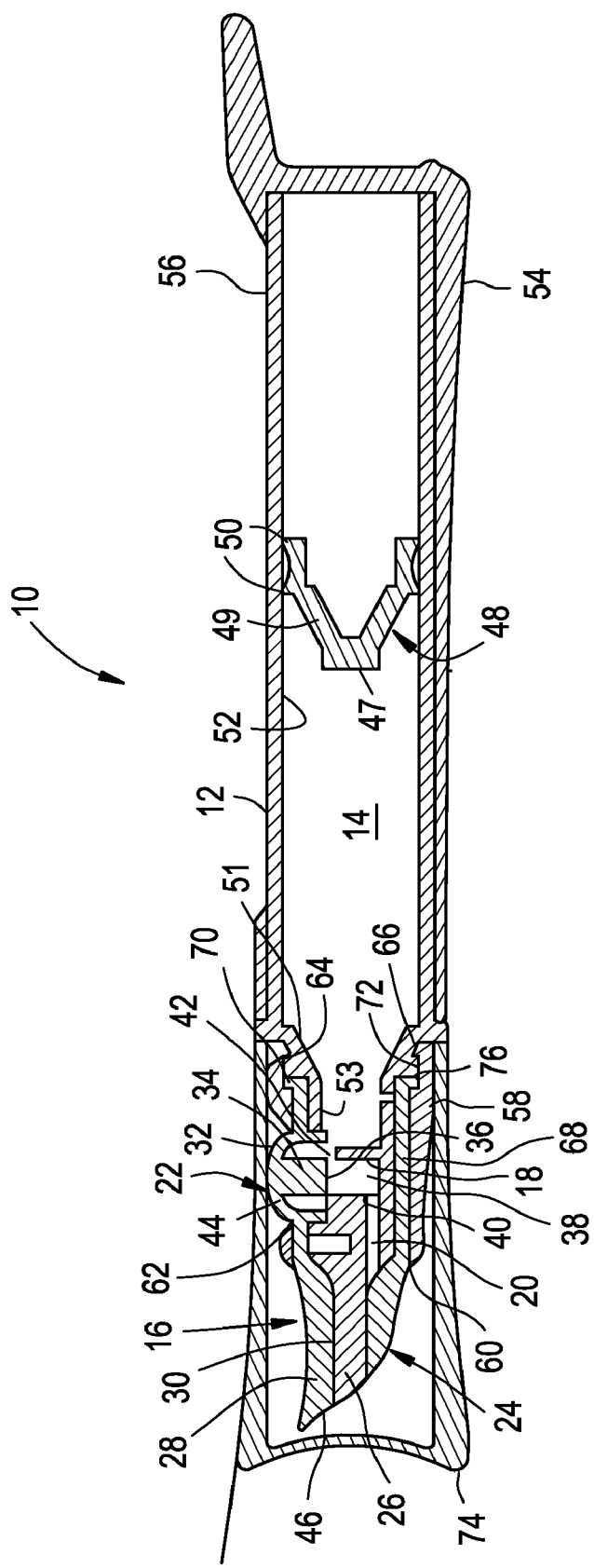
FIG. 1 is a cross-sectional view of a first embodiment of a dispenser, in an unactuated state, which is the rest position.

Referring to FIGS. 1-4, a dispenser embodying the present invention is indicated generally by the reference numeral 10. The dispenser 10 is particularly suitable for dispensing metered amounts of fluids and other substances, such as pharmaceutical, cosmeceutical, cosmetic, and ophthalmic products. However, as may be recognized by those of ordinary skill in the pertinent art based on the teachings herein, the dispenser 10 may be adapted to dispense any of numerous different types of fluids or other substances that are currently known, or that later become known. As shown typically in FIG. 1, the dispenser 10 includes a body 12 defining a variable-volume storage chamber 14 for storing the substance, such as a pharmaceutical, cosmeceutical, cosmetic and ophthalmic product. A dispensing nozzle or portion 16 is connected with the body 12 and defines a bore 18 coupled in fluid communication with the storage chamber 14 for receiving the stored substance therefrom, and at least one outlet aperture 20 coupled in fluid communication with the bore 18. An actuator and piston assembly 22 is receivable within the bore 18, and a dispensing nozzle or one-way valve 24 is mounted on the dispensing portion 16 for dispensing metered amounts of the stored substance therethrough.

The one-way valve 24 includes an axially-extending valve seat 26, and an axially-extending flexible valve cover 28 seated on the valve seat and defining a normally-closed, axially-extending seam 30 therebetween forming a fluid-tight seal between the valve cover 28 and valve seat 26. As described further below, the flexible valve cover 28 is movable relative to the valve seat 26, and the seam 30 is connectable in fluid communication with the outlet aperture 20 to allow the passage of product through the seam and out of the dispenser.

The actuator and piston assembly 22 includes a manually engageable actuator 32, and a piston 34 coupled to the actuator 32 for moving the piston within the bore 18 and dispensing a predetermined amount of product within the bore through the outlet aperture 20 and one-way valve 24. The piston 34 is movable between a first or rest position, as shown typically in FIG. 1, with the piston tip 36 spaced away from the outlet aperture 20 and defining a compression chamber 38 therebetween, and a second fully-activated position, shown typically in FIG. 2, with the piston tip 36 located adjacent to, or in contact with a stop surface 40 formed at the downstream end of the bore 18 for dispensing a predetermined amount of substance within the compression chamber through the outlet aperture 20. As can be seen, the actuator and piston assembly 22 is formed integral with the valve cover 28. In the illustrated embodiment of the present invention, the actuator and piston assembly 22 is molded in one piece with the valve cover 28. As also shown, the actuator 32 is laterally positioned with respect to the one-way valve 24. The piston 34 defines a drive axis extending between the rest position of FIG. 1 and the fully-actuated position of FIG. 2, and the piston drive axis is oriented transverse to the axis of the one-way valve 24 and body 12. In the illustrated embodiment of the present invention, the piston drive axis is oriented at about 90° relative to the axis of the one-way valve and body. However, as described further below, the drive axis may be oriented at any of numerous angular orientations in order to facilitate the manufacture of the dispenser, to facilitate manual manipulation of the dispenser, or otherwise to improve the ergonomics of the dispenser.

As indicated above, the one-way valve 24 includes a relatively rigid valve seat 26 and a flexible valve cover 28 mounted over the valve seat and defining the axially elongated, annular seam or interface 30 therebetween. As described further below, the actuator and piston assembly 22 forces a metered dose of fluid or other substance at sufficient pressure to open the valve (the "valve opening pressure") and force the fluid or other substance through the valve interface 30 and out of the dispenser. The valve cover 28 preferably forms an interference fit with the valve seat 26 to thereby form a fluid-tight seal in the normally closed position and, in turn, maintain the fluid or other substance within the dispenser in a sterile and hermetically sealed condition. As shown typically in FIGS. 1 and 2, the valve cover 28 defines a substantially tapered cross-sectional shape moving in the axial direction from the interior toward the exterior of the valve. This configuration requires progressively less energy to open each respective annular portion of the valve when moving axially from the interior toward the exterior of the valve. Alternatively, or in combination with the tapered valve cover, the valve seat may define an outer diameter that progressively or otherwise increases in the axial direction toward the valve tip, to provide the same or similar effect. As a result, once the base of the valve is opened, the pressure is sufficient to cause the respective axial segments of the valve cover 28 to progressively open and then close after passage of fluid therethrough when moving in the axial direction toward the valve tip to dispense a metered dose. Also, at any time when dispensing a metered dose, preferably any one of a plurality of different substantially annular segments of the valve cover 28 engages the valve seat 26 to maintain a fluid-tight seal across the valve 24, and thereby prevent ingress through the valve of germs, bacteria or other unwanted substances and into the storage chamber 14.

The valve seat 26 and bore 18 are formed integral with the body 12 and are formed of a relatively rigid material. The dosage or compression chamber 38 is formed between the piston tip 36 and a stop surface 40 formed on the axially inner side of the valve seat 26. A fluid passageway 42 extends between the piston tip 36 and the inlet to the bore 18 and, when the piston 34 is located in the rest position, as shown in typically FIG. 1, the fluid passageway 42 is coupled in fluid communication between the dosage chamber 38 and storage chamber 14 for permitting the flow of fluid or other substance from the storage chamber into the dosage chamber.

The bore 18 defines a diameter or width selected to cooperate with the piston tip 36 to define the volume of the dosage chamber 38 and thus the volume of the dosage dispensed. The axial extent of the bore 18 defines a compression zone within which the fluid or other substance is compressed by the piston 34 and, in turn, forced through the one-way valve 24. As described further below, the piston 34 is movable relative to the bore 18 from (i) a rest position, shown typically in FIG. 1, with the piston tip 36 laterally spaced relative to the inlet end of the bore 18 to allow fluid communication between the storage chamber 14, fluid passageway 42, and dosage chamber 38; (ii) to a fully-actuated position, shown typically in FIG. 2, with the peripheral surface of the tip 36 of the piston 34 received within the bore 18 and the distal end of the piston located adjacent to, or in contact with, the stop surface 40 of the bore; and (iii) back again to the rest position of FIG. 1 upon release of the actuator 32. As shown in FIG. 2, the peripheral surface of the piston tip 36 slidably contacts, and preferably forms an interference fit with the bore 18 to thereby form a substantially fluid-tight seal therebetween. However, as indicated further below, such an interference fit or fluid-tight seal may not be required for all embodiments or applications of the dispenser.

In the rest position (FIG. 1) and at the start of the inner stroke of the piston 34 (i.e., in the direction from the inlet of the bore toward the stop surface 40), the compression zone 38 is in fluid communication with the fluid passageway 42 and storage chamber 14, and thus fluid is permitted to flow both forwardly in front of the piston, and rearwardly back over the sides of the piston tip 36. Then, when the sealing surface of the piston tip 36 slidably engages the bore 18, a substantially fluid-tight seal is formed therebetween, trapping a substantially precise volume of fluid within the compression zone 38 and forcing the metered volume of fluid through the valve 24. If desired, the tip of the piston and/or the compression zone may be shaped to facilitate such seal. For example, the tip of the piston may define a substantially frusto-conical, cross-sectional shape. Further, the bore may define a reduced cross-sectional diameter or width forming the compression zone. In addition, the materials of the piston tip and bore may be selected to achieve such characteristics. For example, the piston tip and portion of the bore forming the compression zone may be formed of relatively rigid plastic materials that are dimensioned to form a fluid-tight annular seal when slidably engaging one another.

In the illustrated embodiments of the present invention, the dispenser body is made of a relatively hard plastic material, such as any of the plastics sold under the trademarks Topaz™, Surlyn™, and Zeonex™. The valve cover 28 and integral actuator and piston assembly 22, on the other hand, is preferably made of an elastomeric material that is relatively soft in comparison to the body 12 and valve seat 26. For example, the valve cover 28 and integral actuator and piston assembly 22 may be made of a polymeric material, such as one of the materials sold under the trademarks Kraton™ or Santoprene™ (e.g., Santoprene 8211-35 (shore 35 hardness) or 8211-55 (shore 55 hardness)), or a vulcanized rubber or other polymeric material. In addition, as described further below, in some currently preferred embodiments of the present invention, at least the actuator 32 and/or piston 34 (or a needle penetrable region thereof) is made of a needle penetrable and thermally resealable thermoplastic material. However, as may be recognized by those of ordinary skill in the pertinent art based on the teachings herein, these materials are only exemplary, and numerous other materials that are currently known, or that later become known for performing the functions of the components described herein equally may be used.

As described further below, the illustrated embodiment of the present invention includes a single outlet aperture 20 for delivering the metered dosage. If desired, additional outlet apertures may be added (e.g., a second outlet aperture of the same or different size diametrically opposed to the illustrated aperture 20), or the aperture 20 may be moved to a position other than that shown (e.g., the single outlet aperture may be located on the opposite side of the valve seat relative to that shown).

Figure 2:
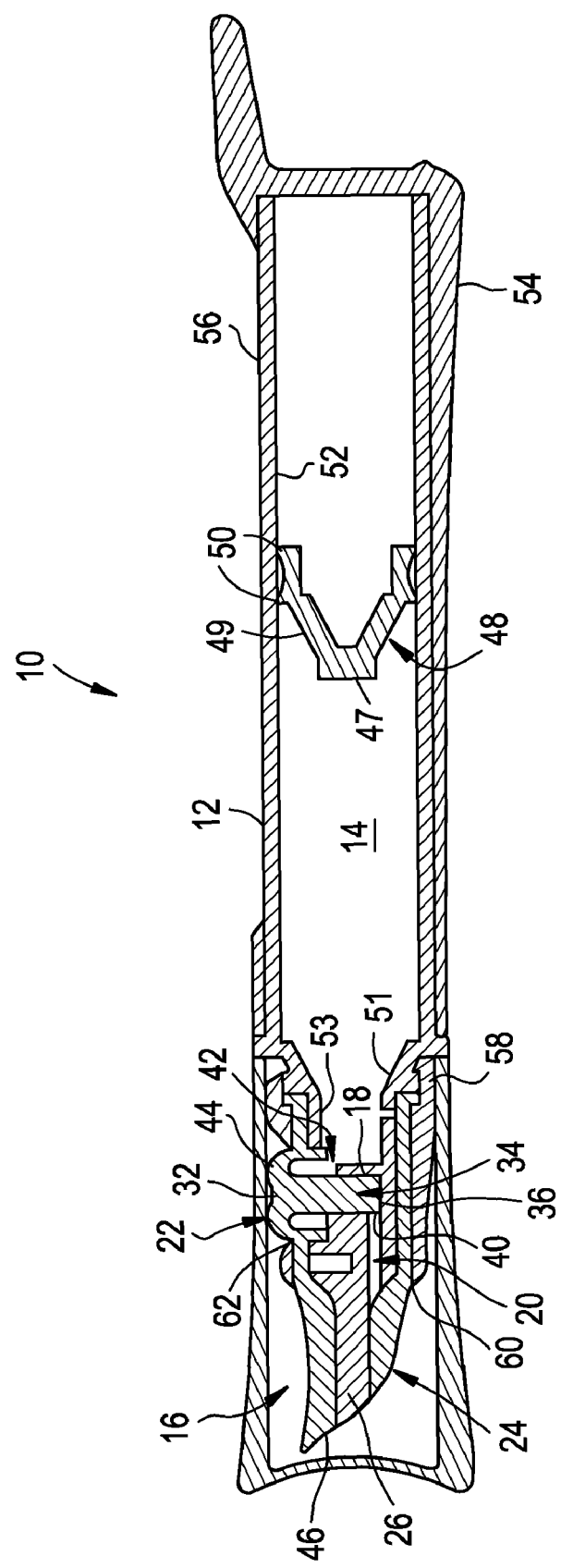
FIG. 2 is a cross-sectional view of the dispenser of FIG. 1 showing the actuator and piston assembly in an actuated state, which is the fully-depressed position.
Figure 3:
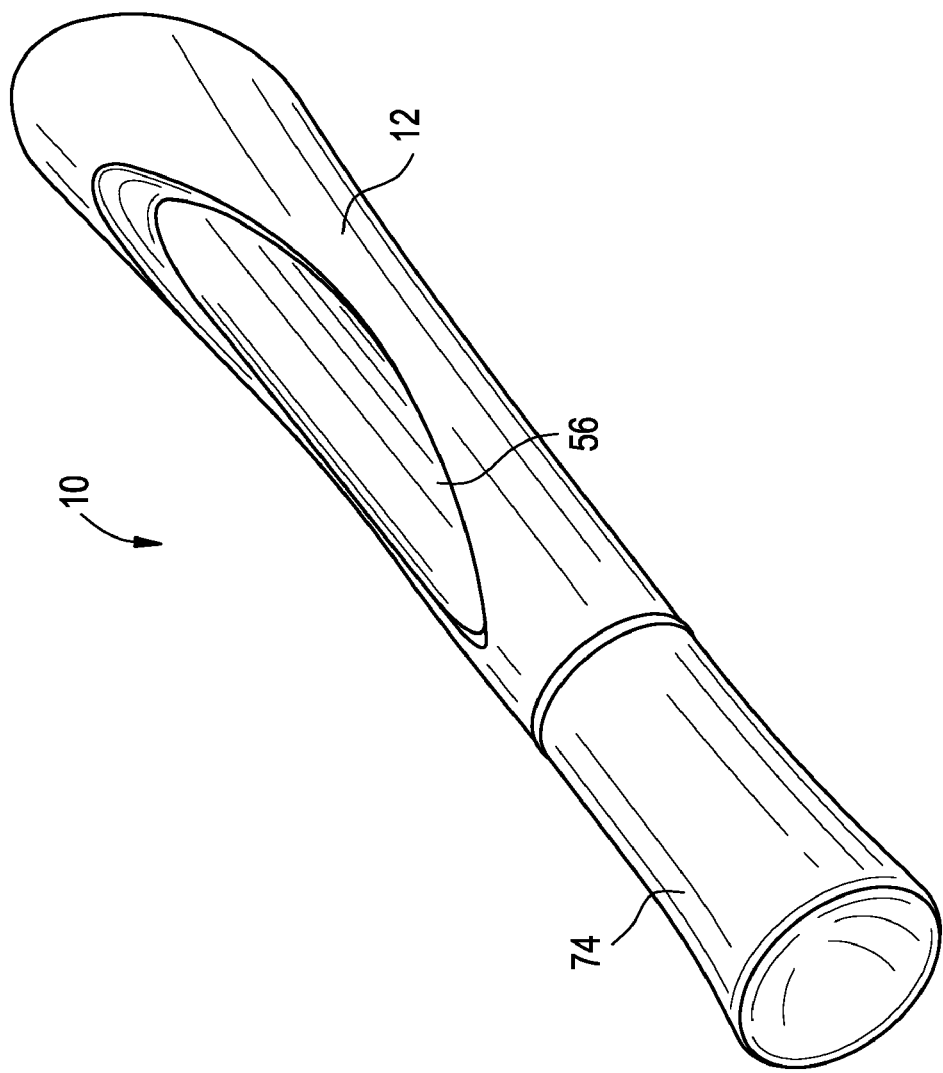
FIG. 3 is a perspective view of the dispenser of FIG. 1.
Figure 4:
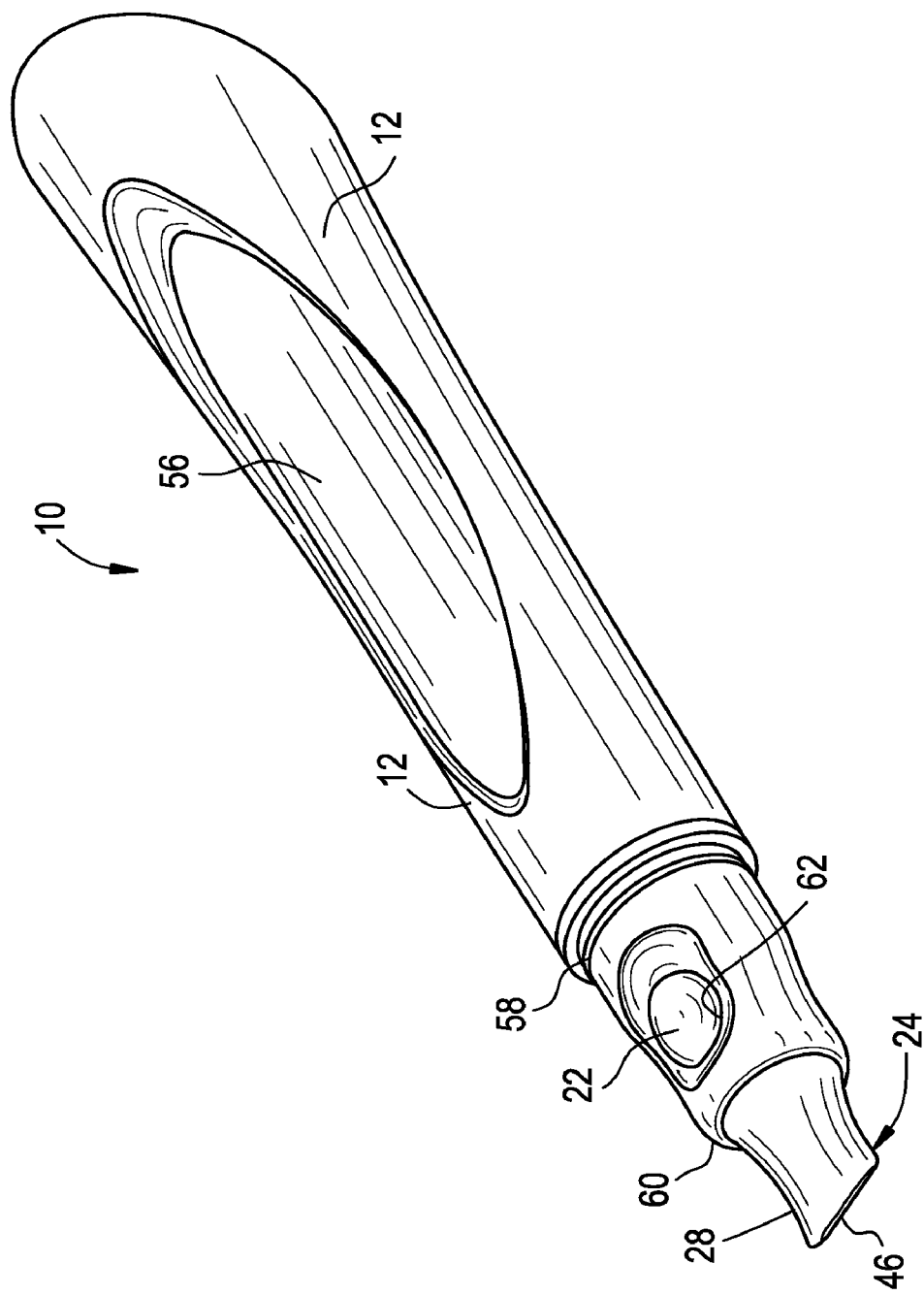
FIG. 4 is a perspective view of the dispenser of FIG. 1 with the cap removed.

As shown in FIG. 2, the manually-engageable actuator 32 defines a substantially-dome shaped spring 44 for normally biasing the piston 32 away from the outlet aperture 20 and into the rest position, as shown in FIG. 1. One advantage of the substantially dome-shaped configuration is that the dome shape imparts lateral (or radial) and axial forces to the piston 34 to facilitate maintaining sufficient force to drive the piston from the fully-actuated position (FIG. 2) to the rest or ambient position (FIG. 1) throughout the shelf-life and usage of the dispenser 10. Yet another advantage of the illustrated embodiment of the present invention is that by forming the spring integral with the actuator and piston, a separate part that otherwise would be required to bias the piston, is eliminated. However, as may be recognized by those of ordinary skill in the pertinent art based on the teachings herein, the integral spring 44 of the actuator 32 may take any of numerous different shapes and/or configurations, and/or may be formed of any of numerous different materials, that are currently known, or that later become known for performing the function of the spring as described herein. For example, the spring may define a shape other than a dome shape, or may not be formed integral with the bladder or the valve member. For example, the spring could take the form of a coil or other type of spring, that may be made of metal, plastic, or any of numerous other materials, for biasing the piston as described herein. Also, the shape and/or material of construction of the spring may be selected to control the spring force applied to the piston.

As indicated in FIG. 2, the manually-engageable portion 32 of the actuator is axially depressible inwardly against the bias of the dome-shaped spring 44 to drive the piston 34 from the rest position shown in FIG. 1 to the fully-actuated position shown in FIG. 2. As described above, this inner stroke of the piston 34 forces a predetermined amount of substance through the one-way valve 24 and onto an applicator surface 46 formed by the distal end portions of the valve cover 28 and valve seat 26. Then, when the user releases the manually-engageable portion 32, the dome-shaped spring 44 drives the piston assembly 34 in a return stroke from the fully-actuated position shown in FIG. 2 to the rest position shown in FIG. 1. On the return stroke, a vacuum is created in the dosage chamber 38, which then pulls the fluid or other substance contained within the storage chamber 14 into the dosage chamber 38 such that the substance flows through the passageway 42 and into the dosage chamber.

As shown, the applicator surface 46 defines a curvilinear contour to substantially conform to the contour of an application surface, such as facial tissue. In the illustrated embodiment, the applicator surface 46 defines a curvilinear contour designed to emulate the tip of a finger, and is particularly suitable for applying an eye shadow, concealer or other cosmetic product, or a dermatological or pharmaceutical product that is applied to the skin. Alternatively, the contour may be shaped to conformably contact a user's lips for purposes of applying a metered dose of liquid lipstick, other cosmetic, pharmaceutical, or other cosmetic substance thereto. For example, the applicator surface may take any of a variety of different forms designed to substantially conformably contact a user's eyelids, eyebrows, eyelashes, cheeks, toenails, fingernails, etc., or to deliver fluids or other substances in a desired manner, such as a desired drop size or in a desired spray pattern. As described further below, the applicator surface may be shaped to effectively deliver ophthalmic products, such as eye drops, in a manner that releases the drop at a substantially predetermined location on the applicator surface, and that allows substantially the entire dosage to be released, to thereby facilitate a substantially consistent drop size or volume from one dosage to the next. Alternatively, as described further below, the dispensing tip may be configured to deliver substances, and preferably metered dosages of such substances, to any desired body surface or cavity, including, for example, dispensing tips that are configured to deliver metered dosages to the nasal, ear (i.e., otic delivery), vaginal, penis and/or anal cavities, dispensing tips configured to deliver metered dosages to the scalp, or dispensing tips configured to deliver metered dosages to fingernails and/or toe nails, including dispensing tips configured to deliver substances underneath the nails, on the tops of the nails, or to the cuticles of the nails. Accordingly, as may be recognized by those of ordinary skill in the pertinent art based on the teachings herein, the specific shape and/or configuration of the dispensing tip and/or of the applicator surface of the dispensing tip may take any of numerous different shapes or configurations that are currently known, or that later become known for performing any of numerous different functions of the dispensing tip or applicator surface of the dispensing tip, and/or to address the requirements of any of numerous different applications of the dispensers for delivering any of numerous different substances that are currently known or that later become known.

One advantage of the currently preferred embodiments of the present invention, is that once a metered dosage is dispensed, the piston tip 36 returns to its rest position, as shown typically in FIG. 1, and thus substantially equalizes the pressure in the compression chamber 38 and the storage chamber 14. As a result, the product does not continue to flow through the valve 24. Thus, residual seepage of the product or other substance through the dispensing valve 24 may be avoided. Yet another advantage of the dispenser of the present invention, is that the bulk of the product remains hermetically sealed in the storage chamber 14 throughout the shelf life and usage of the dispenser. Yet another advantage of the dispensers of the present invention is that the one-way valve 24 substantially prevents any germs, bacteria or other unwanted substances from entering the dispenser and contaminating the bulk of the product contained within the storage chamber 14. Accordingly, if desired, the dispensers of the present invention may be used to store and dispense multiple doses of sterile substances and/or preservative-free substances.

The dispenser 10 further includes a piston or plunger 48 that is slidably received within the body 12 and axially spaced relative to the actuator and piston assembly 22 to define the variable-volume storage chamber 14 therebetween. The plunger 48 includes at least one, and preferably two axially spaced, outer annular sealing members or portions 50 that sealingly engage the inner wall 52 of the body 12 to form a fluid-tight seal therebetween. The sealing members or portions 50 may be formed integral with the plunger 48, such as by forming thereon annular protuberances, as shown, or may be formed by sealing members, such as o-rings or other sealing members, that are received within corresponding grooves or recesses formed in the plunger. As the integral actuator 32 and piston 34 is progressively actuated, the plunger 48 slides forwardly within the dispenser body 12 (or in the direction of right to left in FIGS. 1 and 2) due to the suction forces exerted thereon as the fluid or other stored substance is dispensed from the variable-volume storage chamber 14. The dispenser 10 further includes a casing 54 that substantially encloses the body 12, and defines a substantially oblong or oval window 56 therethrough. In the illustrated embodiment, the body 12 is transparent, or otherwise substantially see-through, to allow a user to look through the window 56 and determine the amount of stored substance remaining within the variable-volume storage chamber 14. The casing 54 and/or body 12 defines one or more apertures (not shown) formed therethrough and located on the opposite side of the plunger 48 relative to the one-way valve 24 to allow the flow of air therethrough and, in turn, permit the plunger 48 to slide inwardly upon dispensing the fluid or other substance from the variable-volume storage chamber 14.

In the illustrated embodiment, the plunger 48 is made of a relatively resilient plastic material, such as one of the plastics sold under the trademark Santoprene™ (e.g., Santoprene 8211-35 (shore 35 hardness) or 8211-55 (shore 55 hardness)). As may be recognized by those of ordinary skill in the pertinent art based on the teachings herein, these materials are only exemplary, and may be changed as desired or otherwise required by a particular application. For example, in applications requiring low sorption, the plunger 48 and dispenser body 12 may be formed of a relatively low sorptive material, such as a relatively hard plastic, including one or more of the plastics sold under the trademark Topaz™. As described further below, the plunger 48 may include a needle penetrable and resealable stopper or like portion that permits the variable-volume storage chamber to be needle filled with a substance therethrough, and that allows the resulting needle hole to be thermally resealed, such as by application of laser energy thereto.

The plunger 48 defines a substantially flat inner surface 47, and a substantially conical tapered portion 49 extending between the inner surface 47 and the annular sealing surfaces 50. As can be seen, the inner end of the body 12 defines a substantially conically-tapered wall 51, and a reduced-diameter portion 53 extending between the conically-tapered wall 51 and the fluid-passageway 42. When the variable-volume storage chamber 14 is substantially emptied of the substance stored therein, the flat surface 47 of the plunger is received within the reduced-diameter portion 53, and the conically-tapered portion 49 is moved axially adjacent to, or into engagement with the conically-tapered wall 51 of the body 12. One advantage of this configuration is that it substantially eliminates any dead volume in the dispenser and thus any waste of product stored therein.

The dispenser 10 further comprises an approximately annular securing member 58 coupled to the body 12 and fixedly securing the valve cover 28 thereto. The securing member 58 defines a first aperture 60 on one end thereof, and a second aperture 62 located laterally respect to the first aperture 60 and extending through a side wall thereof. The one-way valve 24 extends through the first aperture 60, and the manually-engageable portion 32 of the actuator 22 and integral dome spring 44 extend laterally through the second aperture 62. As shown in FIG. 1, the securing member 58 includes an annular, tapered flange 64 that projects radially inwardly on the inner end of the securing member, and the body 12 defines a corresponding annular groove 66 that receives therein the annular tapered flange 64 to fixedly secure the securing member to the body. The annular base portion 68 of the flexible valve cover 28 extends axially between the securing member 58 and the body 12, and includes an annular flange 70 on the inner end thereof that is received within a corresponding annular groove 72 formed in the securing member 58 to fixedly secure the flexible valve cover 28 to the body 12. A substantially cylindrical cap 74 is slidably received over the one-way valve 24 to enclose the dispensing tip during non-use. As can be seen, the securing member 58 defines on its inner end a peripheral lobe 76 that is received within a corresponding annular groove formed on the interior of the cap 74 to releaseably secure the cap to the body 12. As may be recognized by those of ordinary skill in the pertinent art based on the teachings herein, the securing member 58 may be formed integral with the valve cover 28 and actuator and piston assembly 22 such that all components are molded in one piece, or alternatively, the securing member may be over-molded to the valve cover actuator and piston assembly (or vice versa).

As may be recognized by those of ordinary skill in the pertinent art based on the teachings herein, the variable-volume storage chamber 14 may be formed in any of numerous different ways that are currently known, or that later become known, including, for example, by using a relatively flexible bladder mounted within a relatively rigid body, or by using a collapsible tube. The variable-volume storage chambers formed with a flexible bladder may be constructed in accordance with the teachings of the following co-pending patent application which is assigned to the Assignee of the present invention, and is hereby expressly incorporated by reference as part of the present disclosure: U.S. application Ser. No. 10/843,902, filed May 12, 2004, titled "Dispenser and Apparatus and Method for Filling a Dispenser".

Similarly, the variable-volume storage chambers formed by a collapsible tube may be constructed in accordance with the teachings of the following co-pending patent applications which are assigned to the Assignee of the present invention, and are hereby expressly incorporated by reference as part of the present disclosure: U.S. patent application Ser. No. 10/640,500, filed Aug. 13, 2003, entitled "Container And Valve Assembly For Storing And Dispensing Substances, And Related Method," U.S. patent application Ser. No. 29/174,939, filed Jan. 27, 2003, entitled "Container and Valve Assembly," U.S. patent application Ser. No. 29/188,310, filed Aug. 15, 2003, entitled "Tube and Valve Assembly," U.S. patent application Ser. No. 29/191,510, filed Oct. 7, 2003, entitled "Container and Valve Assembly," U.S. Patent Application Ser. No. 60/528,429, filed Dec. 10, 2003, entitled "Valve Assembly And Tube Kit For Storing And Dispensing Substances, And Related Method," and U.S. Patent Application Ser. No. 60/539,602, filed Jan. 27, 2004, entitled "Tubular Container And One-Way Valve Assembly For Storing And Dispensing Substances, And Related Method."

Figure 5:
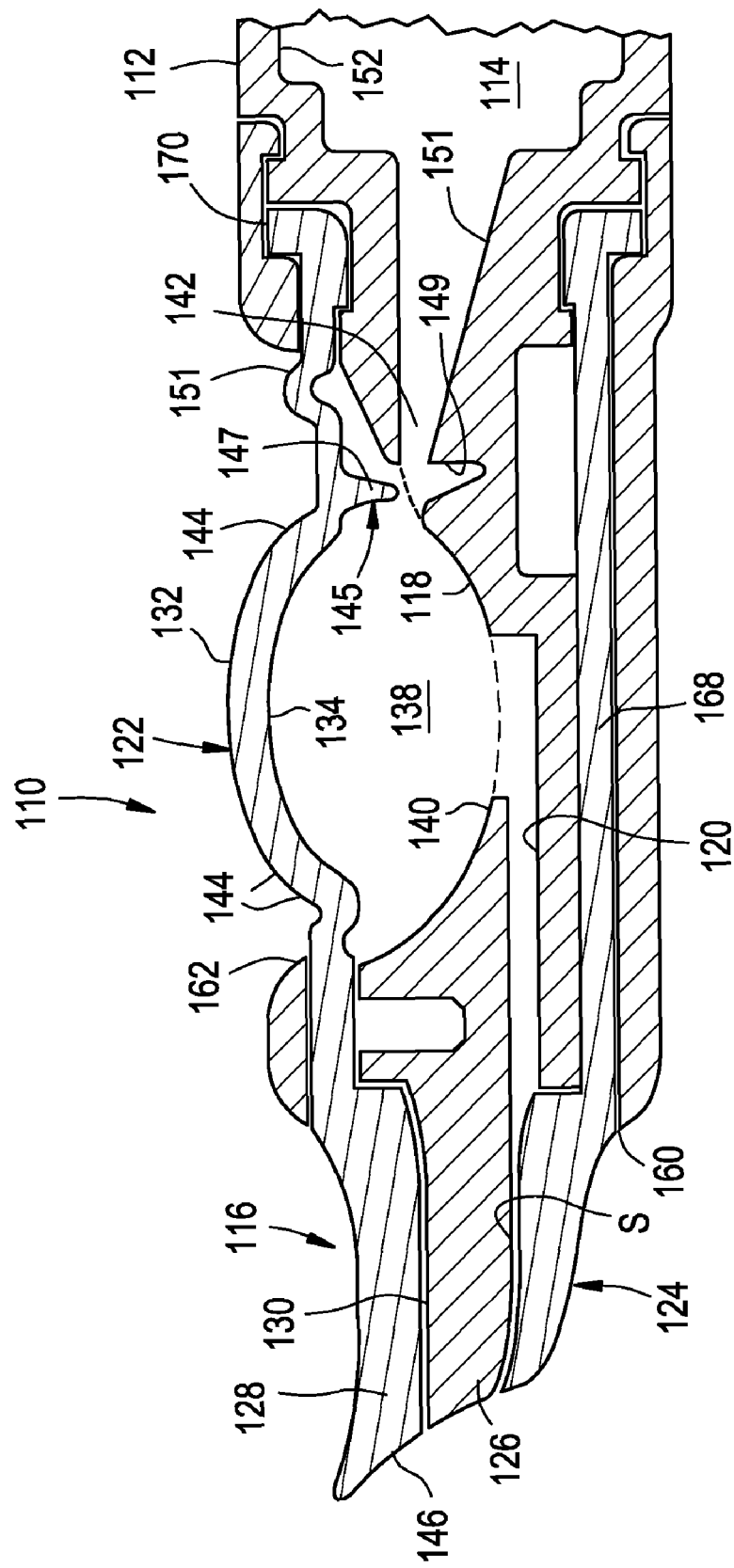
FIG. 5 is a partial, cross-sectional view of a second embodiment of a dispenser.
Figure 6:
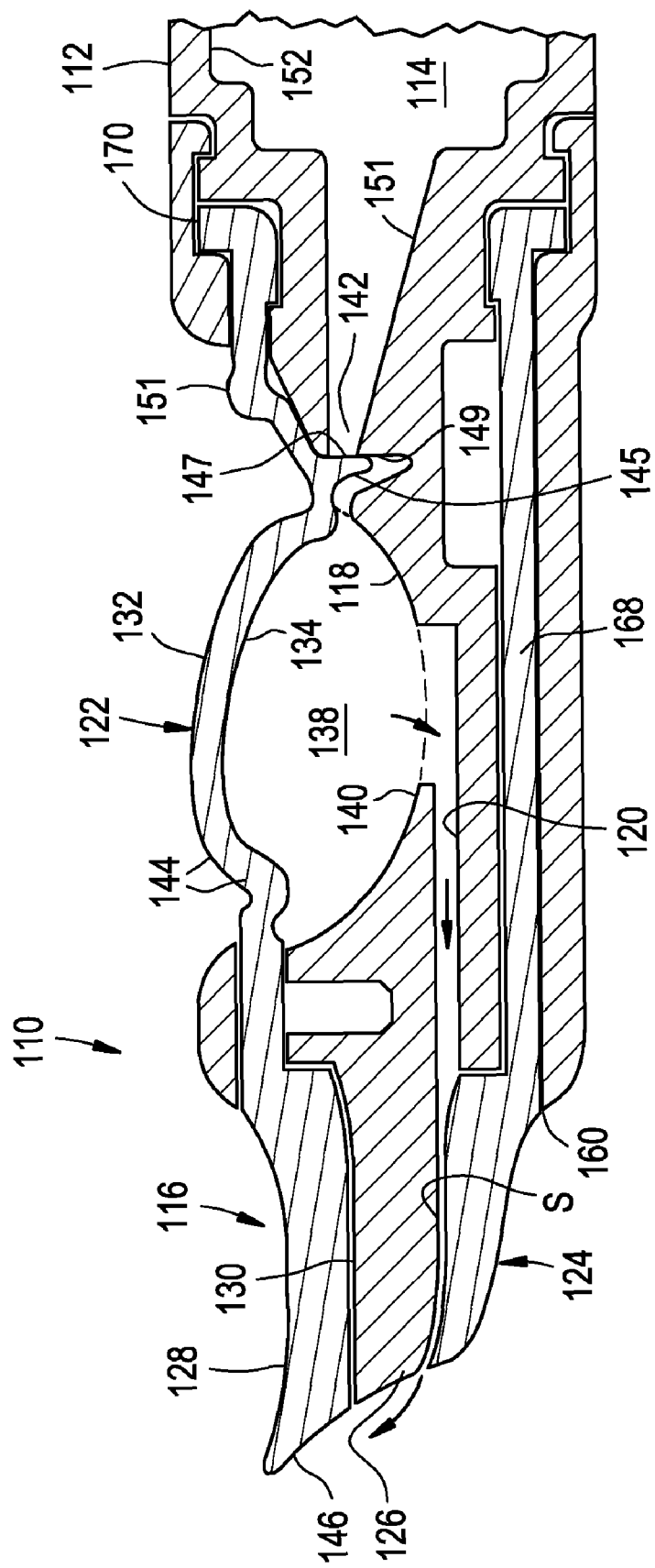
FIG. 6 is a partial, cross-sectional view of the dispenser of FIG. 5 showing the actuator and piston assembly in a partially actuated position.
Figure 7:
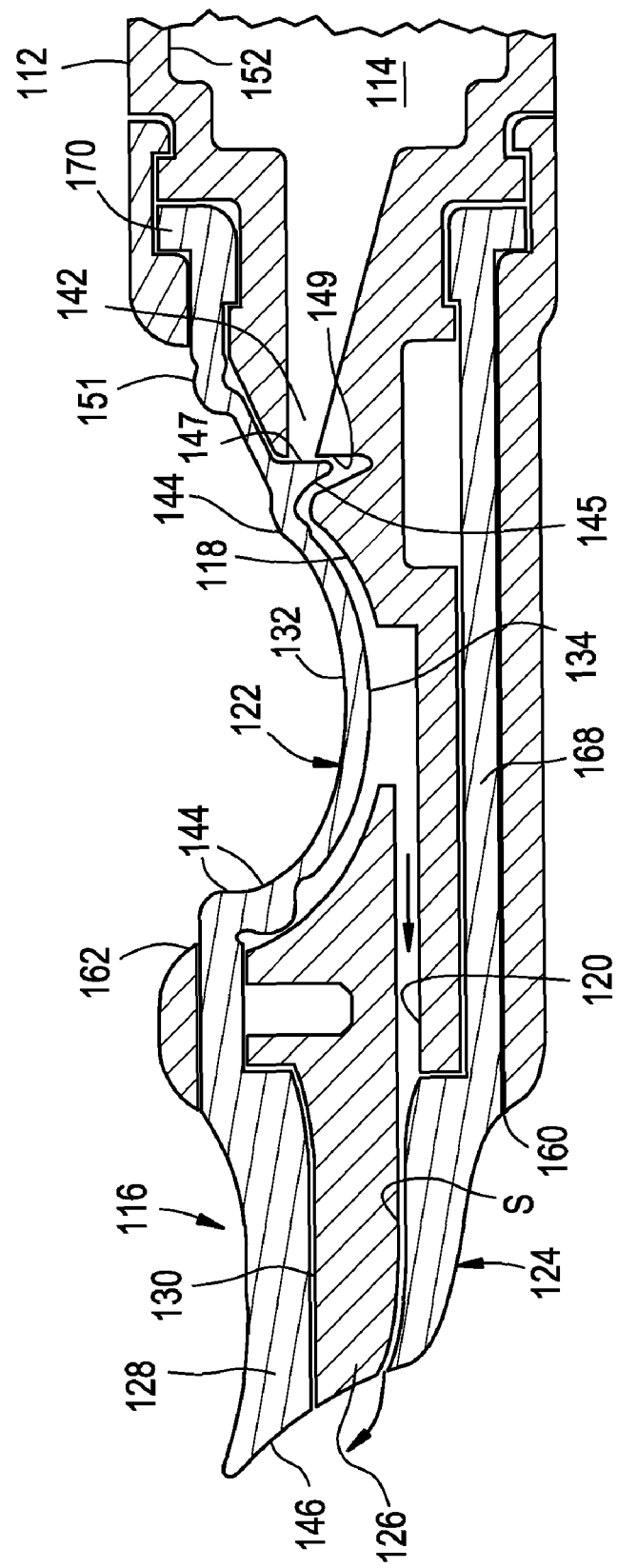
FIG. 7 is a partial, cross-sectional view of the dispenser of FIG. 5 showing the actuator and piston assembly in a fully-actuated position.

In FIGS. 5-7, another dispenser embodying the present invention is indicated generally by the reference numeral 110. The dispenser 110 is substantially similar to the dispenser 10 described above with reference to FIGS. 1-4, and therefore like reference numerals preceded by the numeral "1" are used to indicate like elements. A primary difference of the dispenser 110 in comparison to the dispenser 10 described above is in the shape and configuration of the piston 134 and bore 118. As can be seen, the bore 118 is not substantially cylindrical as described above, but rather is defined by a substantially concave recess. Similarly, the piston 134 is defined by the underside of the dome-shaped actuator 132. Accordingly, as shown typically in FIGS. 6 and 7, when a user manually depresses the dome-shaped actuator 132, the underside 134 thereof functions as a piston and, in turn, pressurizes the substance within the compression chamber 138 and forces same through the one-way valve 124. Accordingly, in the rest or ambient position, as shown typically in FIG. 5, the underside 134 of the manually-engageable actuator 132 is spaced away from the stop surface 140 and defines a substantially concave shape as shown. Then, as shown typically in FIGS. 6 and 7, in order to dispense a metered dose, the actuator 132 is manually depressed until the underside 134 is located adjacent to, or in contact with the stop surface 140 at the base of the substantially concave bore 118. In the fully-actuated position, and as shown typically in FIG. 7, the central portion of the actuator 132 is substantially inverted.

The actuator and piston assembly 122 also includes an anti-reflux valve 145 to prevent substance within the compression chamber 138 from flowing back into the variable-volume storage chamber 114 after depressing the actuator. As can be seen, the anti-reflux valve 145 is defined by a laterally projecting lobe 147 formed on the opposite side of the piston or underside 134 relative to the one-way valve 124, and a corresponding recess 149 formed in the body 112 at the junction of the bore 118 and fluid-passageway 142. As can be seen, as the actuator 132 is manually depressed, the lobe or flexible valve member 147 of the anti-reflux valve 145 is received within the recess or valve seat 149 to seal the compression chamber 138 with respect to the variable-volume storage chamber 114, and thereby prevent any substance from flowing in the direction from the compression chamber 138 back into the variable-volume storage chamber 114 during the compression stroke of the actuator. A curvilinear buffer spring 151 is formed opposite the lobe 147 and spaced axially between the lobe and flange 170 to allow the dome spring 144 to elongate itself during the compression stroke of the actuator and facilitate the return of the dome spring from the fully-actuated position (FIG. 7) to the rest or ambient position (FIG. 5).

When the user releases the actuator 132, the substantially dome-shaped spring portion 144 thereof drives the actuator 132 and underside 134 thereof into the ambient or rest position, as shown typically in FIG. 5. In the rest or ambient position of FIG. 5, the substance in the variable-volume storage chamber 114 is drawn through the tapered channel 151 and passageway 142 and into the compression chamber 138 to fill the compression chamber for the next dose.

Another difference of the dispenser 110 in comparison to the dispenser 10 is that the valve cover 128 and corresponding surface of the valve seat 126 define a substantially sigmoidal surface contour at the valve seam 130 in order to facilitate forming a reduced cross-sectional thickness of the valve cover 128 at the dispensing tip and to direct the dispensed substance toward the central region of the applicator surface 146.

In a currently preferred embodiment of the present invention, the actuator 32, 132 may be formed of a needle penetrable and resealable material in order to allow the dispenser 110 to be needle filled with the substance to be stored therein, and resealed, in accordance with the teachings of the co-pending patents and patent applications incorporated by reference below. During filling, it may be desirable to insert the filling needle through a central portion of the dome-shaped actuator 132, and to then slightly withdraw the needle prior to or during filling, in order to substantially maintain the concave or dome shape of the actuator, and to maintain the anti-reflux valve 145 open, during filling. Alternatively, the plunger 148 (not shown) may include a needle penetrable and resealable stopper or like portion that permits the variable-volume storage chamber 114 to be needle filled with a substance therethrough, and that allows the resulting needle hole to be thermally resealed, such as by application of laser energy thereto. Accordingly, the needle penetrable and resealable portion of the actuator and piston assembly, the valve cover and actuator and piston assembly, and/or the plunger or resealable stopper or like portion thereof, may be formed with any of the various materials disclosed in, and may be needle filled and resealed in accordance with the various teachings of, the following patents and co-pending patent applications that are assigned to the Assignee of the present invention and are hereby expressly incorporated by reference as part of the present disclosure: U.S. Pat. No. 6,604,561, entitled "Medicament Vial Having a Heat-Sealable Cap, and Apparatus and Method for Filling the Vial"; U.S. Pat. No. 6,684,916, entitled "Medicament Vial Having a Heat-Sealable Cap, and Apparatus and Method for Filling the Vial"; U.S. patent application Ser. No. 10/694,364, filed Oct. 27, 2003, entitled "Medicament Vial Having a Heat-Sealable Cap, and Apparatus and Method for Filling the Vial"; U.S. patent application Ser. No. 10/766,172, filed Jan. 28, 2004, entitled "Medicament Vial Having a Heat-Sealable Cap, and Apparatus and Method for Filling the Vial"; U.S. patent application Ser. No. 10/600,525, filed Jun. 19, 2003, entitled "Sterile Filling Machine Having Needle Filling within E-Beam Chamber"; U.S. patent application Ser. No. 10/655,455, filed Sep. 3, 2003, entitled "Sealed Containers and Methods of Making and Filling Same"; U.S. provisional patent application Ser. No. 60/518,685, filed Nov. 10, 2003, entitled "Needle Filling and Laser Sealing Station"; and U.S. patent application Ser. No. 11/070,440, filed Mar. 2, 2005, entitled "Apparatus for Needle Filling and Laser Resealing".

FIGS. 8-9 illustrate another dispenser embodying the present invention and indicated generally by the reference numeral 210. The dispenser 210 is substantially similar to the dispenser 10 described above with reference to FIGS. 1-7, and therefore like reference numerals preceded by the numeral "2" are used to indicate like elements.

The dispenser 210 includes a body 212 defining a variable-volume storage chamber 214 for storing a fluid or other substance, such as a pharmaceutical, cosmeceutical, cosmetic, or ophthalmic product. A dispensing nozzle or portion 216 is connected with the body 212 and defines a bore 218 coupled in fluid communication with the storage chamber 214 for receiving the stored substance therefrom, and at least one outlet aperture 220 coupled in fluid communication with the bore 218. An actuator and piston assembly 222 is receivable within the bore 218, and a dispensing nozzle or one-way valve 224 is mounted on the dispensing portion 216 for dispensing metered amounts of the stored substance therethrough. A fluid passageway 242 extends between the piston tip 236 and the inlet to the bore 218 and, when the piston 234 is located in the rest position, as shown in typically FIG. 9, the fluid passageway 242 is coupled in fluid communication between the dosage chamber 238 and storage chamber 214 for permitting the flow of fluid or other substance from the storage chamber into the dosage chamber.

The one-way valve 224 includes an axially-extending valve seat 226, and an axially-extending flexible valve cover 228 seated on the valve seat and defining a normally-closed, axially-extending seam 230 therebetween forming a fluid-tight seal between the valve cover 228 and valve seat 226. As described further below, the flexible valve cover 228 is movable relative to the valve seat 226, and the seam 230 is connectable in fluid communication with the outlet aperture 220 to allow the passage of product through the seam and out of the dispenser.

The dispensing nozzle 216 includes a tip portion 231 configured to provide a substantially consistent dosage volume (or size) that is released into a user's eyes throughout usage of the dispenser. As shown in FIGS. 8 and 9, the end face 233 of the valve seat 226 is formed at an acute angle relative to the axis of the one-way valve 224, and the axial end portion 229 of the valve cover 228 extends axially outwardly of the end face 233 of the valve seat. In an exemplary embodiment, the angle of the end face 233 is approximately 30°; however, as may be recognized by those of ordinary skill in the pertinent art based on the teachings herein, this angle may be changed as desired or otherwise required by a particular application. The axially outermost point 235 of the valve seat 226 is coincident with the outlet opening 220 through which each metered dosage is released from the dispenser. Also at this location, the valve cover 228 forms a substantially pointed tip 231 that, as shown best in FIG. 9, is pointed substantially radially inwardly.

One advantage of the pointed tip 231 is that it presents a substantially reduced surface area in contact with each metered dosage upon being dispensed through the outlet aperture 220 which, in turn, reduces the surface tension between the dosage and the tip, and thereby facilitates release of substantially the entire metered dosage from the tip. Yet another advantage of this configuration is that it substantially prevents, or at least substantially reduces the formation of dosage residue at the tip. Yet another advantage is that the pointed tip configuration 231 in combination with the piston 234 and dosage chamber 238 provides a predetermined, substantially consistent and repeatable dose volume (or size) that is released from the dispenser and into a user's eyes or other target region. Yet another advantage of the illustrated tip configuration is that the hoop stress of the valve cover 228 is reduced at the region of the tip 231 (where the valve cover is not fully annular) which, in turn, reduces the velocity of the fluid dispensed through the valve 224. This, in combination with the radially curved nature of the tip 231 substantially prevents the dosage from being released in a spray, but rather facilitates in allowing the drop to be released from the pointed tip 231 in drop form. Still another advantage of the illustrated tip configuration is that the pointed tip 231 is pointed substantially radially inwardly, thereby presenting a rounded, and substantially blunt tip to the user's eyes or other target region, while simultaneously providing a pointed surface region on the radial inner side of the rounded tip that facilitates in releasing substantially the entire metered dosage on a consistent and repeatable basis. Yet another advantage of the illustrated dispenser is that each dose is released at substantially the same location (i.e., from the pointed tip 231) thus allowing a user to consistently hold the dispenser in the same orientation, and accurately deliver the drops to the eyes or other target region in a repeatable manner.

The actuator and piston assembly 222 includes a manually engageable actuator 232, and a piston 234 formed integral with the actuator 232 for moving the piston within the bore 218 and dispensing a predetermined amount of product within the bore through the outlet aperture 220 and one-way valve 224. The piston 234 is movable between a first or rest position, as shown in FIG. 9, with the piston tip 236 spaced away from the outlet aperture 220 and defining a compression chamber 238 therebetween that is coupled in fluid communication with the variable-volume storage chamber 214 through the fluid passageway 242, and a second fully-activated position (not shown, however, see FIG. 2) with the piston tip 236 located adjacent to, or in contact with a stop surface 240 formed at the downstream end of the bore 218 for dispensing a predetermined amount of substance within the compression chamber through the outlet aperture 220. As can be seen, the actuator and piston assembly 222 is formed integral with the valve cover 228. In the illustrated embodiment of the present invention, the actuator and piston assembly 222 is molded into one piece with the valve cover 228. As also shown, the actuator 232 is laterally positioned with respect to the one-way valve 224. In the illustrated embodiment of the present invention, the piston drive axis is oriented at about 90° relative to the axis of the one-way valve and body. However, as indicated above, this angle may be changed as desired or as may be required by a particular application. The dispenser 210 operates in a similar manner and is made of the same or similar materials as the dispenser 10, as described above.

The dispenser 210 further includes a piston or plunger 248 that is slidably received within the body 212 and axially spaced relative to the actuator and piston assembly 222 to define the variable-volume storage chamber 214 therebetween. The plunger 248 includes an annular sealing member 250 that engages the inner wall 252 in at least one and preferably two axially-spaced locations. The sealing member 250 sealingly engages the inner wall 252 of the body 212 to form a fluid-tight seal therebetween. The plunger 248 also includes a re-sealable stopper or portion 251 that is needle penetrable to fill the variable-volume storage chamber 214 and is laser re-sealable to hermetically seal the resulting needle hole, as described further below.

The dispenser 210 further comprises an approximately annular securing member 258 that is relatively rigid in comparison to the valve cover to prevent the valve cover 228 from expanding radially where the securing member overlies the valve cover. In addition, the securing member 258 prevents the valve cover 228 from being removed, and otherwise prevents the hermetic seal between valve cover and body from being tampered with. In one embodiment of the dispenser 210, the valve cover 228 and securing member 258 are formed by over molding, and the sealing member 250 and resealable stopper 251 of the plunger likewise are formed by over molding. More particularly, in one embodiment of the present invention, the securing member 258 is injection molded in a first mold cavity. Then, the securing member 258 is robotically transferred to a second mold cavity, and the valve cover 228 is injection over molded over the securing member in the second mold cavity. If desired, the valve cover may be over molded to the securing member in the same mold (or vice versa) to avoid the need to robotically or otherwise transfer a part from one mold to another prior to over molding. Similarly, the sealing member 250 is molded in a first mold cavity, and a second mold insert or cavity is then employed in the same mold to over mold the resealable stopper 251 to the respective sealing member and thereby form the plunger 248.

Preferably, each mold includes multiple mold cavities for simultaneously molding and over molding multiple parts. In one embodiment of the present invention, the body 212 forming the variable-volume storage chamber 214 and relatively rigid valve seat 226 is injection molded at substantially the same time as the over molded securing member 258 and valve cover 228, and the plunger 248. Then, the over molded securing member and valve cover are robotically assembled to the valve seat 226 end of the body 212 while at least part of the body is located in its respective mold and preferably at bactericidal temperature (i.e., a temperature that is sufficiently high to kill any germs thereon), and the plunger 248 is robotically assembled to the other end of the body 212 while at least part of the body is located in its respective mold and preferably at bactericidal temperature. The molding and assembly is preferably performed under a substantially laminar flow of filtered sterile air or other gas to maintain aseptic conditions. This type of molding and assembly process is described in further detail in U.S. patent application Ser. No. 60/660,935, filed Mar. 11, 2005, entitled "Apparatus and Method for Aseptically Molding and Assembling Containers with Heated Surfaces, and Filling Same," which is assigned to the Assignee of the present invention and is hereby expressly incorporated by reference as part of the present disclosure.

Alternatively, the body 212, over molded securing member 258 and valve cover 228, and plunger 248 may be molded in separate injection molding machines, the parts then may be assembled robotically or otherwise in a commercially clean environment, and the assembled, sealed empty dispensers then may be sterilized, such as by the application of radiation thereto, including for example gamma radiation, and then needle filled and laser resealed in the manner generally described in the patent and patent applications incorporated by reference above.

In the illustrated embodiment, the sealing member 250 is made of a relatively resilient plastic material, such as one of the plastics sold under the trademark Santoprene™ (e.g., Santoprene 8211-35 (shore 35 hardness) or 8211-55 (shore 55 hardness)). As may be recognized by those of ordinary skill in the pertinent art based on the teachings herein, these materials are only exemplary, and may be changed as desired or otherwise required by a particular application. For example, in applications requiring low sorption, the sealing member 150 and dispenser body 112 may be formed of a relatively low sorptive material, such as a relatively hard plastic, including one or more of the plastics sold under the trademark Topaz™.

In addition, the re-sealable stopper 251 is formed of a thermoplastic material defining a needle penetration region that is pierceable with a needle to form a needle aperture therethrough, and is heat re-sealable to hermetically seal the needle aperture by applying laser radiation at a predetermined wavelength and power thereto. The stopper 251 includes a thermoplastic body defining (i) a predetermined wall thickness in an axial direction thereof, (ii) a predetermined color and opacity that substantially absorbs the laser radiation at the predetermined wavelength and substantially prevents the passage of the radiation through the predetermined wall thickness thereof, and (iii) a predetermined color and opacity that causes the laser radiation at the predetermined wavelength and power to hermetically seal the needle aperture formed in the needle penetration region thereof in a predetermined time period and substantially without burning the needle penetration region (i.e., without creating an irreversible change in molecular structure or chemical properties of the material). In some embodiments, the predetermined time period is approximately 2 seconds, is preferably less than or equal to about 1.5 seconds, and most preferably is less than or equal to about 1 second. In some of these embodiments, the predetermined wavelength of the laser radiation is about 980 nm, and the predetermined power of each laser is less than about 30 Watts, and preferably less than or equal to about 10 Watts, or within the range of about 8 to about 10 Watts. Also in some of these embodiments, the predetermined color of the material is gray, and the predetermined opacity is defined by a dark gray colorant (or pigment) added to the stopper material in an amount within the range of about 0.3% to about 0.6% by weight.

In addition to the thermoplastic materials described above, the thermoplastic material of the stopper 251 may be a blend of a first material that is preferably a styrene block copolymer, such as the materials sold under either the trademarks KRATON or DYNAFLEX, such as DYNAFLEX G2706-10000-00, or GLS 230-174 (Shore A=30), and a second material that is preferably an olefin, such as the materials sold under either the trademarks ENGAGE or EXACT, such as EXACT 8203, or GLS 230-176 (Shore A=42). In some embodiments, the first and second materials are blended within the range of about 50:50 by weight to preferably about 90:10 by weight, and most preferably about 90:5 by weight (i.e., first material:second material). The benefits of the preferred blend over the first material by itself are improved water or vapor barrier properties, and thus improved product shelf life; improved heat sealability; a reduced coefficient of friction; improved moldability or mold flow rates (which is discussed below); and a reduction in hysteresis losses.

Alternatively, the thermoplastic material of the re-sealable stoppers 251 may take the form of a styrene block copolymer sold by GLS Corporation of McHenry, Ill. under the designation LC 254-071. This type of styrene block copolymer compound exhibits approximately the following physical properties: (i) Shore A Hardness: about 28-29; (ii) Specific Gravity: about 0.89 g/cm$^3$; (iii) Color: approximately grey to dark grey; (iv) 300% Modulus, flow direction: about 181-211 psi; (v) Tensile Strength at Break, flow direction: about 429-498 psi; (vi) Elongation at Break, flow direction: about 675%-708%; and (vii) Tear Strength, flow direction: about 78-81 lbf/in.

In each of these embodiments of the present invention, the predetermined color and opacity of the thermoplastic is defined by a grey colorant that is provided in an approximately 3% color concentrate (i.e., there is an approximately 33:1 ratio of the concentrate to the natural resin or TPE). The color concentrate contains about 88.83% carrier or base resin, the remainder is pigment, and the pigment is grey carbon black. Thus, the pigment is about 0.34% by weight of the resulting thermoplastic.

In addition, if desired, a lubricant of a type known to those of ordinary skill in the pertinent art may be added to or included within each of the above-mentioned thermoplastic compounds, in order to prevent or otherwise reduce the formation of particles upon penetrating the needle penetration region of the thermoplastic stopper with a needle or other filling member. In one embodiment of the present invention, the lubricant is a mineral oil that is added to the styrene block copolymer or other thermoplastic compound in an amount sufficient to prevent, or substantially prevent, the formation of particles upon penetrating same with the needle or other filling member. In another embodiment, the lubricant is a silicone, such as the liquid silicone sold by Dow Corning Corporation under the designation "360 Medical Fluid, 350 CST," or a silicone oil, that is added to the styrene block copolymer or other thermoplastic compound in an amount sufficient to prevent, or substantially prevent, the formation of particles upon penetrating same with the needle or other filling member. In one such embodiment, the silicone oil is included in an amount within the range of about 0.4% to about 1% by weight, and preferably within the range of about 0.4 to about 0.6% by weight, and most preferably within the range of about 0.51 or about 0.5% by weight.

Alternatively, the resealable stopper or like portions of the dispenser may be made with one or more of the materials disclosed in international PCT patent application no. PCT/EP2004/008703, (WO2005/014419 A1), filed Aug. 2, 2004, which claims priority to Great Britain patent application no. 031824.25, filed Aug. 4, 2003, each of which is hereby incorporated by reference as part of the present disclosure.

After needle filling the storage chamber 214 through, and laser resealing the stopper 251 of the plunger 248, a cap 253 is fixedly secured to the open end of the body 212 to prevent access to the interior of the body. The cap 253 includes one or more vent apertures (not shown) to prevent the formation of a vacuum between the plunger 248 and cap 253, and otherwise to allow the plunger 248 to freely travel through the body 212 upon dispensing the substance from the storage chamber 214.

FIGS. 10 and 11 illustrate another dispenser embodying the present invention and indicated generally by the reference numeral 310. The dispenser 310 is substantially similar to the dispenser 210 described above with reference to FIGS. 1-9, and therefore like reference numerals preceded by the numeral "3" are used to indicate like elements. In particular, the main difference between dispenser 310 and dispenser 210 is that the piston 334 is angled as compared to the piston 234 (in FIG. 9). As shown, the piston 334 is angled approximately 20° relative to a normal to the axis of the body 312. The piston 334 is angled to assist in the molding of the valve cover 328. The angle can range from approximately 10° to approximately 40°, and most preferably from approximately 20° to approximately 30°. In this embodiment, the tip 331 of the dispenser is shaped to be more pointed rather than rounded. As can be seen, the axially outermost portion 331 extends axially outwardly relative to the adjacent surface 335 of the valve seat 326, but does not curve radially inwardly as in the dispenser 210 of FIGS. 8 and 9. As with the dispenser 210 above, the axially-extending tip 331 is designed to facilitate release of the drop and to prevent the drop from rolling back onto the valve face 333. It is noted that any shape that facilitates the release of the drop, a reduction in drop residue on the tip, and a consistent and repeatable dosage volume (or size) that is released into the eye, is contemplated.

Figure 12:
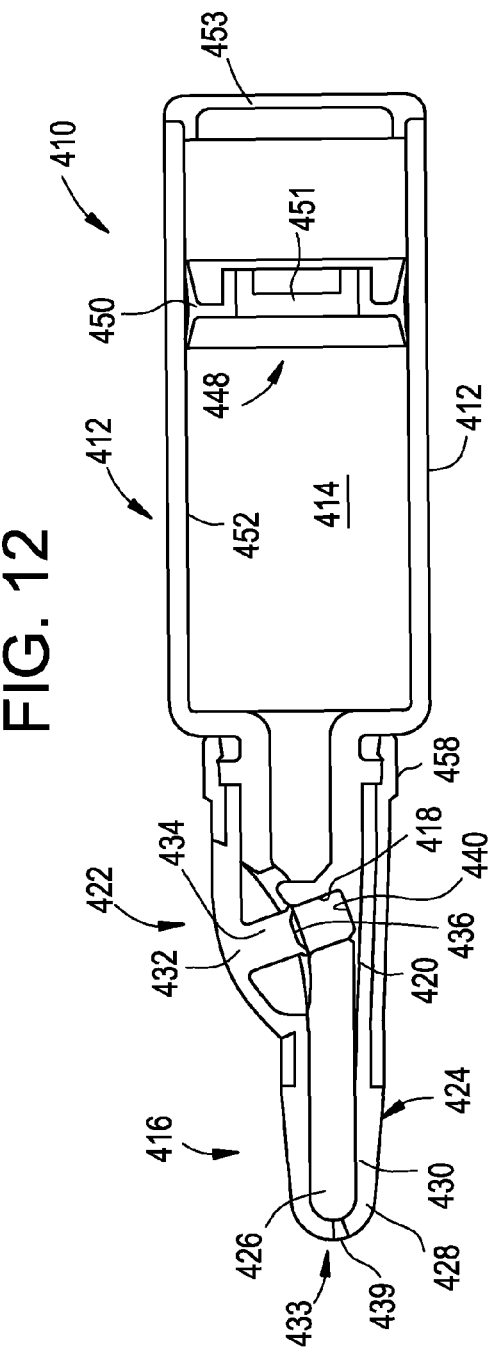
FIG. 12 is a cross-sectional view of a fifth embodiment of a dispenser.
Figure 13:
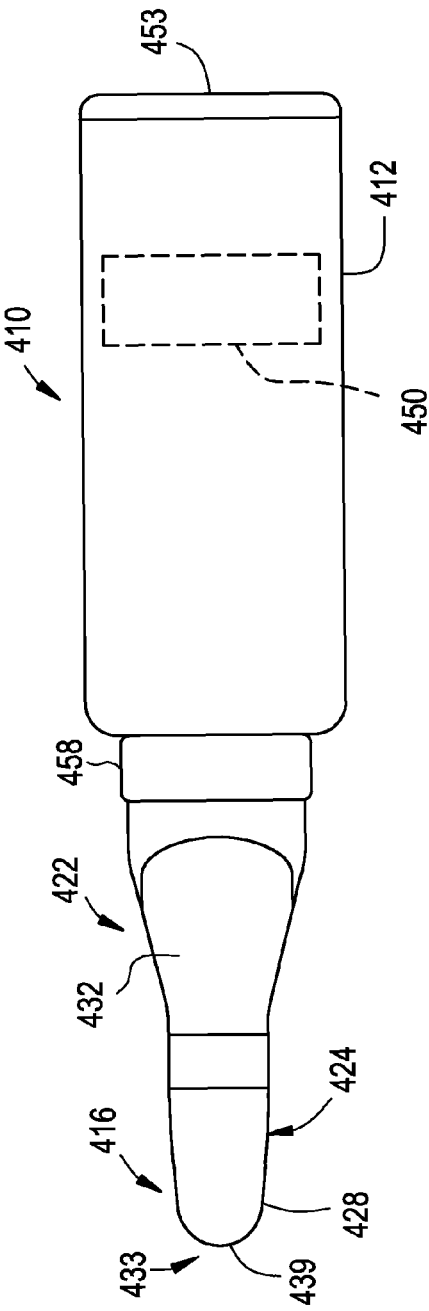
FIG. 13 is a top view of the dispenser of FIG. 12.

FIGS. 12 and 13 illustrate another dispenser embodying the present invention and indicated generally by the reference numeral 410. The dispenser 410 is substantially similar to the dispensers 10, 110, 210, and 310 described above with reference to FIGS. 1-11, and therefore like reference numerals preceded by the numeral "4" are used to indicate like elements.

The primary difference of the dispenser 410 in comparison to the dispensers described above is that the entire end 433 of the dispensing nozzle is rounded and has an opening 439 for dispensing metered drops or dosages therethrough. In addition, the piston tip 436 is shaped to facilitate the formation of a fluid-tight seal between the tip of the piston 434 and the bore 418 and to, in turn, facilitate in dispensing the metered dosages of substance through the outlet aperture 420. Exemplary materials for the actuator 432 includes Rimflex A/AS 25C and Dynaflex G2706, for the securing member 458 includes Alathon H5112 and Profax SR 549, for the annular sealing member 450 includes Huntsman LDPE2053 and Bormed LE6603-PH, and for the body 412 includes Zeonor 750R (COC), Eastar EN067 (PET), and Barex 210 (Acrylic). These materials are equally applicable for any of the embodiments of the dispensers disclosed herein. As will be recognized by those of ordinary skill in the pertinent art based on the teachings herein, however, these materials are only exemplary, and numerous other materials that are currently known, or that later become known, equally may be employed. As with the embodiment illustrated in FIG. 9, the dispenser 410 or select components or subassemblies thereof can be formed through molding and overmolding processes as described above. The dispenser 410 is particularly suited for delivering metered dosages to the eye or ear, but alternatively may be used to deliver metered dosages to any of a variety of other target areas, such as for oral, nasal, vaginal or anal delivery.

Figure 14:
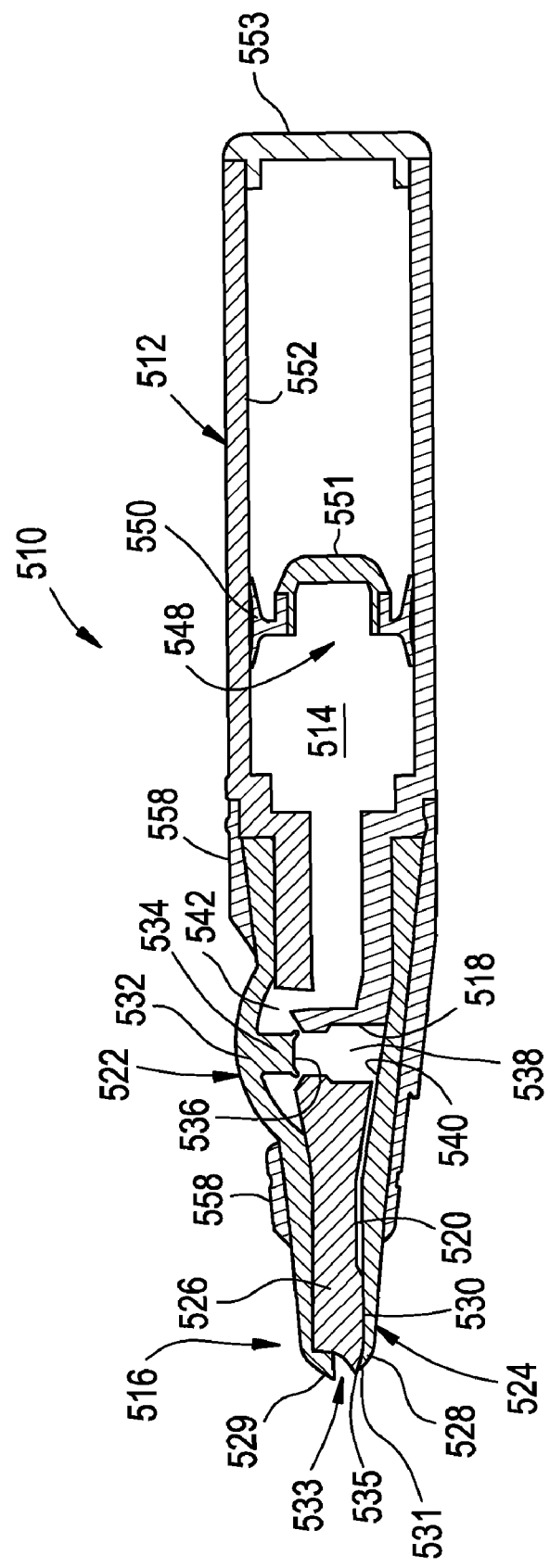
FIG. 14 is a cross-sectional view of a sixth embodiment of a dispenser.

In FIG. 14, another dispenser embodying the present invention is indicated generally by the reference numeral 510. The dispenser 510 is substantially similar to the dispenser 10 described above, and therefore like reference numerals preceded by the numeral "5" are used to indicate like elements. The dispenser 510 is particularly suited for delivering ophthalmic substances, such as eye drops. The primary difference of the dispenser 510 in comparison to the dispensers disclosed above is the configuration of the dispensing nozzle 516. As can be seen, the axial end portion 529 of the valve cover 528 extends radially inwardly over the axial end face 533 of the valve seat 526, and covers a substantial portion of the axial end face. In the illustrated embodiment, the axial end portion 529 of the valve cover 526 covers about one-half of the surface area of the axial end face 533 and extends axially outwardly relative to the other portions of the valve cover and valve seat to thereby present a substantially rounded, blunt dispensing tip. The dispensing aperture 520 is aligned with the axial end portion 535 of the valve seat 526 and dispensing tip 531 of the valve cover 528 to dispense the metered dosages of substance therethrough. As can be seen, and in the same manner or similar to that of the dispensing tips 231 and 331 described above, the tip 531 defines a dispensing region or point of substantially reduced surface area for facilitating the release of metered dosages of substance therefrom, and to prevent dosage residue from collecting thereon. The relatively blunt and rounded axially outermost point 529 of the valve cover 528, on the other hand, protects the eye or other target area from the pointed tip 531. As can be seen, the dispensing tip of the dispenser 510 is particularly suited for delivered metered dosages of substances to a user's eye; however, as with other dispensers disclosed herein, the dispenser 510 equally may be used to deliver metered dosages of substances to other target areas, such for delivery nasally, anally, vaginally, to the penis, or for otic delivery.

Figure 15:
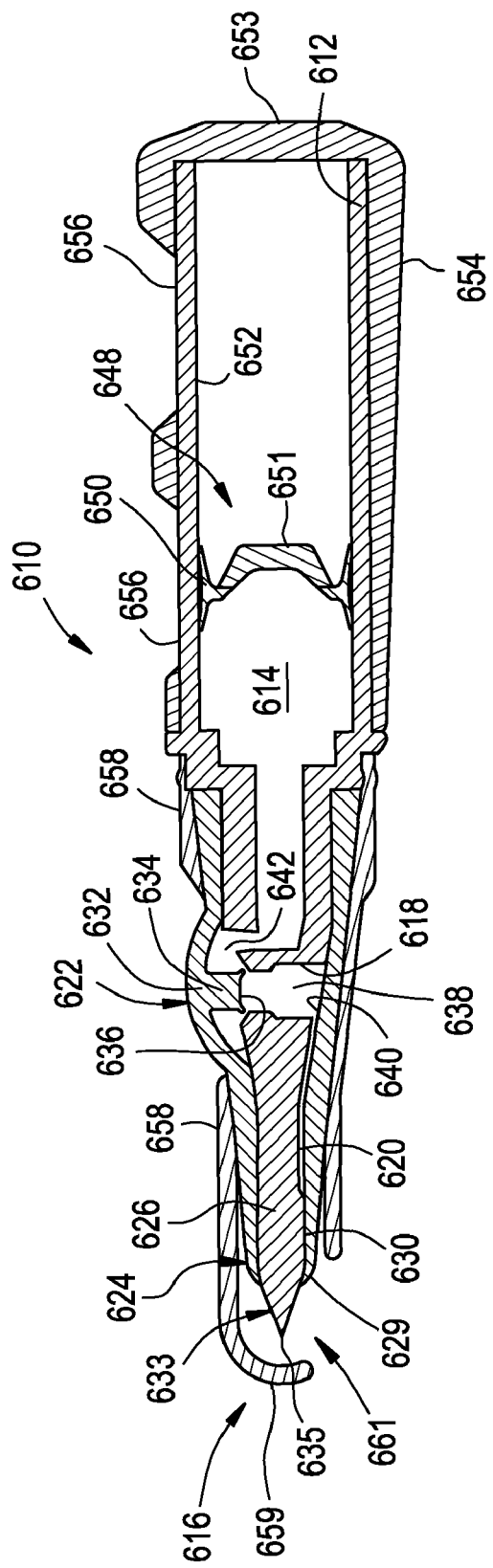
FIG. 15 is a cross-sectional view of a seventh embodiment of a dispenser.

In FIG. 15, another dispenser embodying the present invention is indicated generally by the reference numeral 610. The dispenser 610 is substantially similar to the dispenser 10 described above, and therefore like reference numerals preceded by the numeral "6" are used to indicate like elements. The dispenser 610 is particularly suited for delivering ophthalmic substances, such as eye drops, but alternatively may be used to deliver metered dosages to other target areas. The primary difference of the dispenser 610 in comparison to the dispensers disclosed above is the configuration of the dispensing tip 616. As can be seen, the end face 633 of the valve seat 626 extends axially outwardly of the valve cover 624, and defines a conical surface that terminates in a conically-pointed tip 635. The pointed tip 635 defines a dispensing surface of reduced surface area to facilitate releasing the metered dosages and substance therefrom, and to prevent the collection of dosage residue thereon. The dispensing tip 616 is further defined by the axially outermost end portion 659 of the securing member 658 that forms a rounded, blunt dispensing tip that extends axially outwardly of, and radially over the conically pointed tip 635 to prevent the pointed tip from contacting a user's eye. The end portion 659 of the dispensing tip 616 defines a dispensing aperture 661 that is aligned with the outlet aperture 620 of the one-way valve 624 to permit the metered dosages of substance released from the conically-pointed tip 635 to be dispensed therethrough and directed onto the target area, such as a user's eye.

Figure 16:
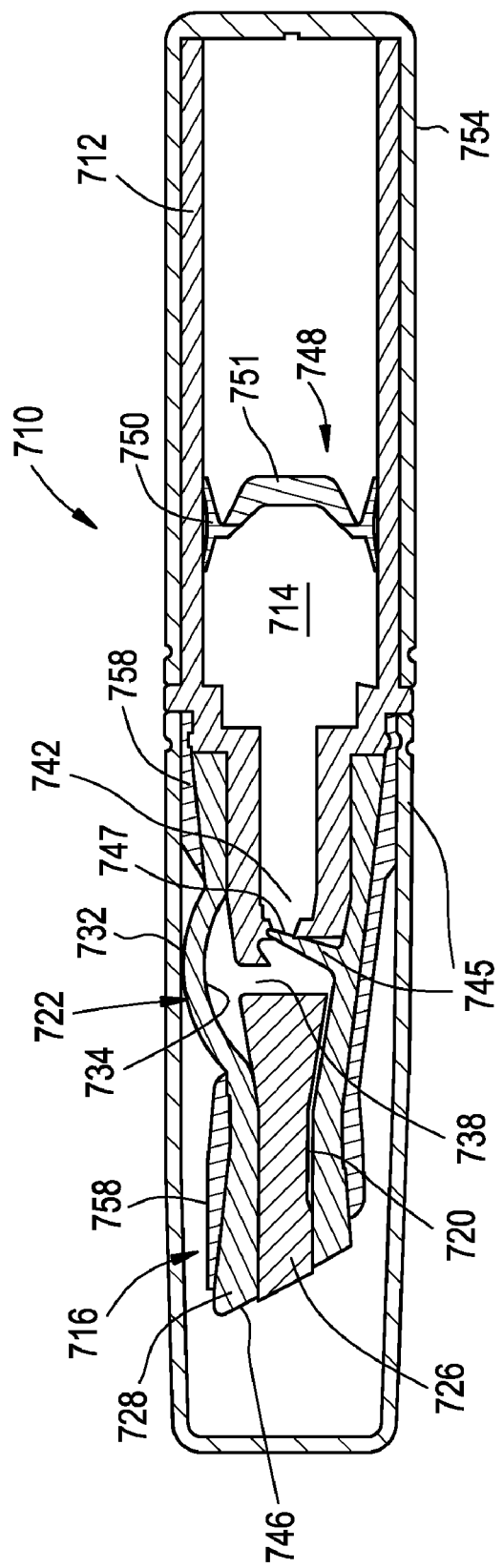
FIG. 16 is a cross-sectional view of an eighth embodiment of a dispenser.

In FIG. 16, another dispenser embodying the present invention is indicated generally by the reference numeral 710. The dispenser 710 is substantially similar to the dispenser 110 described above with reference to FIGS. 5-7, and therefore like reference numerals preceded by the numeral "7" instead of the numeral "1" are used to indicate like elements. The dispenser 710 is particularly suited for delivering pharmaceutical, dermatological, cosmeceutical, and cosmetic substances, such as creams, gels, and other substances. The primary difference of the dispenser 710 in comparison to the dispensers disclosed above is the configuration of the dispensing tip 716. As can be seen, the securing member 758 extends axially outwardly adjacent to the axially outermost end of the valve cover 728 to protect the valve cover and prevent tampering therewith. In addition, as shown typically in FIG. 16, the outlet aperture 720 may be defined by an axially-extending groove formed within the valve seat 726 to facilitate the flow of creams, gels or other relatively viscous substances therethrough, and to control the location at which the metered dosages are dispensed on or through the applicator surface 746. Preferably, an annular space (not shown) is formed between the axially outermost end of the valve cover 728 and the securing member 758 to permit the valve cover to move radially outwardly toward the adjacent wall of the securing member during dispensing of dosages therethrough. In contrast to the embodiment of FIGS. 5-7, the anti-reflux valve 745 is formed by a lobe 747 extending radially upwardly from the opposite side of the valve cover 728 relative to the integral actuator and piston 722, and to the rearward side of the compression chamber 738. As may be recognized by those of ordinary skill in the pertinent art based on the teachings herein, although the cross-sectional thickness of the valve cover 728 is shown as increasing in thickness in the axial direction toward the dispensing tip, the valve cover equally may decrease in thickness as in the other embodiments disclosed herein, and/or the valve seat 726 may increase in diameter or width in the axial direction toward the dispensing tip, to facilitate the dispensing of metered dosages outwardly through the one-way valve and prevent any ingress of substances in the opposite direction.

Figures 17, 18, 19:
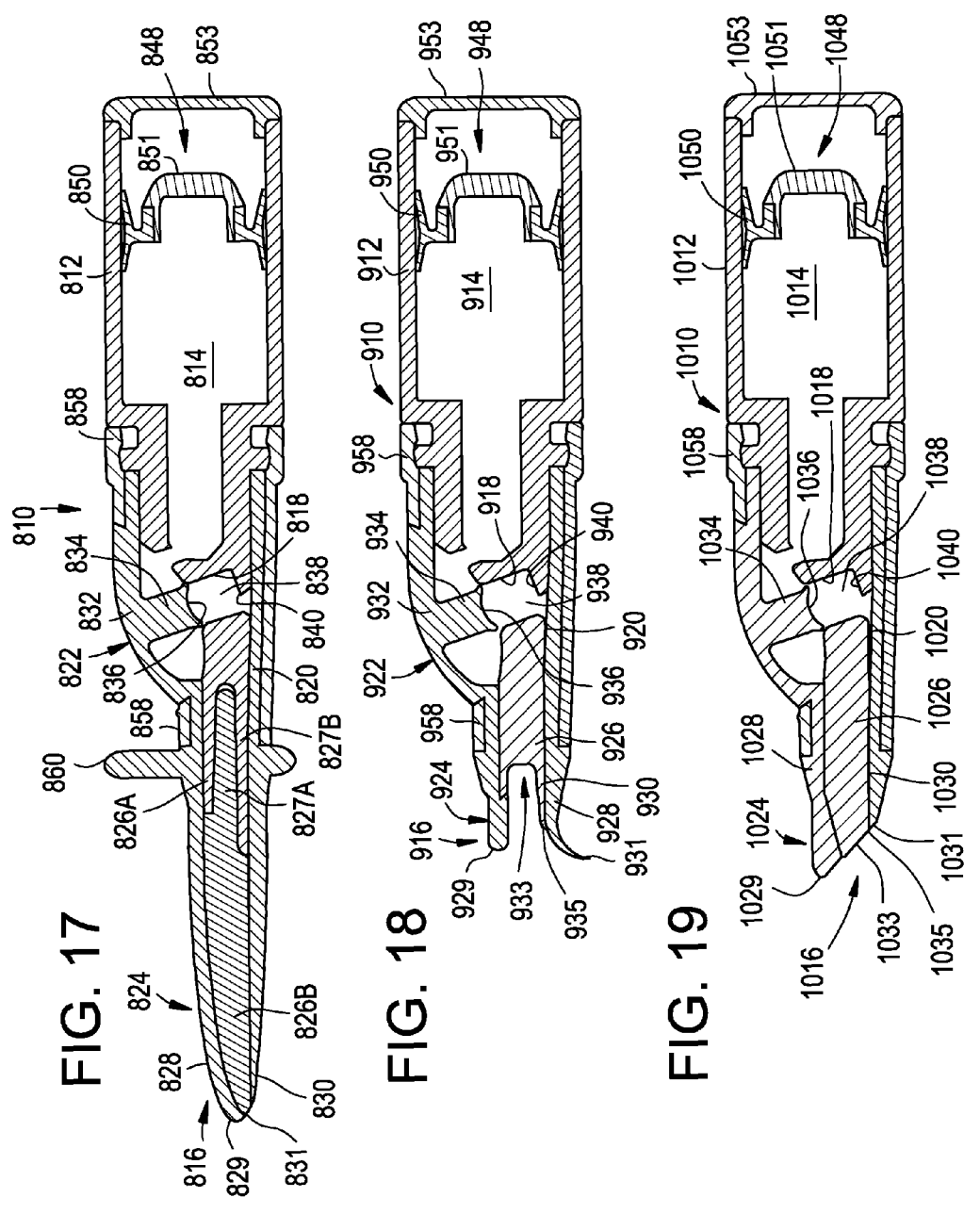

In FIG. 17, another dispenser embodying the present invention is indicated generally by the reference numeral 810. The dispenser 810 is substantially similar to the dispenser 10 described above, and therefore like reference numerals preceded by the numeral "8" are used to indicate like elements. The dispenser 810 is particularly suited for delivering substances to the ear (i.e., otic delivery) but alternatively may be used to deliver metered dosages to other target areas. The primary difference of the dispenser 810 in comparison to the dispensers disclosed above is the configuration of the dispensing tip 816. As can be seen, the dispensing tip 816 is significantly elongated in comparison to the other dispensing tips illustrated herein, and defines an axial length at least several times greater than (e.g., at least about 3 to 5 times greater than) its diameter or width. As also shown, the dispensing tip 816 tapers inwardly toward the tip to facilitate insertion of the tip into an ear or other target cavity or region. If desired, and as shown in FIG. 17, the valve seat 826 may be formed in two parts, 826A and 826B, that are fixedly secured to each other. In the illustrated embodiment, the first valve seat part 826A includes a male fastening portion 827A, and the second valve seat part 826B includes a female fastening portion 827B that receives the male fastening portion. The male and female fastening portions 827A and 827B, respectively, may be interconnected by a mechanical interlock, such as a snap engagement formed, for example, by a radially projecting male lobe(s) and corresponding female recess(es), by welding, such as ultrasonic or spin welding, adhesives, or any of numerous other connecting mechanisms that are currently known or that later become known for performing this function. The integral valve cover 828 and actuator 822 further defines a radially-projecting lobe 860 formed between the valve cover 828 and lateral actuator 822. As shown in FIG. 17, the portion of the lobe adjacent to, or located on the same side of the dispenser 810 as the actuator 822 extends radially outwardly to a greater extent than the diametrically opposed portion of the lobe. The lobe 860 may function as a finger stop, and also as a stop to prevent further insertion of the dispensing tip 816 into the ear or other target cavity or region. One advantage of forming the valve seat 826 in two parts is that it enables the dispensers of the present invention to be manufactured to include any of a variety of different types of dispensing tips while nevertheless allowing such different dispensers to share common components, such as bodies, plungers, etc.

In FIG. 18, another dispenser embodying the present invention is indicated generally by the reference numeral 910. The dispenser 910 is substantially similar to the dispenser 210 described above with reference to FIGS. 8 and 9, and therefore like reference numerals preceded by the numeral "9" instead of the numeral "2" are used to indicate like elements. As with the dispenser 210 described above, the dispenser 910 is particularly suited for delivering substances to the eye, but alternatively may be used to deliver metered dosages to other target areas. The primary difference of the dispenser 910 in comparison to the dispensers disclosed above is the configuration of the dispensing tip 916. As can be seen, the dispensing nozzle 916 includes a tip portion 931 configured to provide a substantially consistent dosage volume (or size) that is released into a user's eyes or other target region throughout usage of the dispenser. The end face 933 of the valve seat 926 is recessed inwardly relative to the axial outermost portions of the one-way valve 924, and the axial outermost point 925 of the valve seat tapers inwardly to a substantially pointed distal region defining a very narrow cross-sectional thickness. The axially outermost point 935 of the valve seat 926 also is coincident with the outlet opening 920 through which each metered dosage is released from the dispenser. Accordingly, the valve seat 926 defines a relatively small surface area at the dispensing location of the metered dosages to thereby prevent the formation of dosage residue due to surface tension on the valve seat and, in turn, facilitate the provision of substantially consistent dosage volumes throughout usage of the dispenser. Also at the dispensing location, the valve cover 928 forms a substantially pointed tip 931 that curves radially outwardly from the outermost point 935 of the valve seat. Similar to the valve seat 925, the tip 931 of the valve cover 928 tapers inwardly to a substantially pointed distal region defining a very narrow cross-sectional thickness. As a result, the tip 931 of the valve cover 928 defines a relatively small surface area at the dispensing location of the metered dosages to thereby prevent the formation of dosage residue due to surface tension on the valve tip and, in turn, facilitate the provision of substantially consistent dosage volumes throughout usage of the dispenser.

Accordingly, the pointed tip 931 presents a substantially reduced surface area in contact with each metered dosage upon being dispensed through the outlet aperture 920 which, in turn, reduces the surface tension between the dosage and the tip, and thereby facilitates release of substantially the entire metered dosage from the tip. As a result, the tip configuration preferably substantially prevents, or at least substantially reduces the formation of dosage residue at the tip. Yet another advantage is that the pointed tip configuration in combination with the piston and dosage chamber provide a predetermined, substantially consistent and repeatable dose volume (or size) that is released from the dispenser and into a target region, such as an eye. Yet another advantage of the illustrated tip configuration is that the hoop stress of the valve cover 928 is reduced at the region of the tip 931 (where the valve cover is not fully annular) which, in turn, reduces the velocity of the fluid dispensed through the valve 924. This, in combination with the radially curved nature of the tip 931 substantially prevents the dosage from being released in a spray, but rather facilitates in allowing the dose to be released from the pointed tip 931 in drop form and into a user's eye or other target region. Still another advantage of the illustrated tip configuration is that the pointed tip 931 is pointed substantially radially outwardly away from the axis of the dispenser, thereby presenting the rounded, and substantially blunt tip 929 to the user's eye or other target region, while simultaneously providing a pointed surface region on the radial outer side of the tip to facilitate releasing substantially the entire metered dosage on a consistent and repeatable basis. Yet another advantage of the illustrated dispenser is that each dose is released at substantially the same location (i.e., from the pointed tip 931) thus allowing a user to consistently hold the dispenser in the same orientation, and accurately deliver the drops to the eyes or other target region in a repeatable manner.

In FIG. 19, another dispenser embodying the present invention is indicated generally by the reference numeral 1010. The dispenser 1010 is substantially similar to the dispensers described above with reference to FIGS. 8 through 14, and therefore like reference numerals preceded by the numeral "10" are used to indicate like elements. As with many of the dispensers described above, the dispenser 1010 is particularly suited for delivering substances to the eye, but alternatively may be used to deliver metered dosages to other target areas, such as the ear. A primary difference of the dispenser 1010 in comparison to the dispensers disclosed above is the configuration of the dispensing tip 1016. As can be seen, the valve seat 1026 defines an angled end face 1033, a substantially thicker valve cover portion 1029 located diametrically opposite the dispensing location 1035 of the valve seat, and a substantially thinner valve cover portion 1031 located at the dispensing location 1035 of the valve seat. As shown in FIG. 19, the upper region of the valve cover 1028 in the drawing both progressively expands radially outwardly and progressively tapers radially inwardly in the direction toward the axially-outermost point 1029, and the upper region of the valve seat 1026 in the drawing tapers radially inwardly in the direction toward the axially-outermost point of the valve seat, to thereby progressively increase the hoop stress in the valve cover 1028 when moving through the valve cover axially outwardly in this thickened region of the valve cover. On the diametrically opposite side of the valve cover 1028 (or the lower portion of the valve cover in the drawing), on the other hand, the valve cover tapers radially inwardly toward the axially-outermost point or dispensing location 1035, and the valve seat 1026 neither tapers inwardly or outwardly in this region. As a result, the hoop stress in the valve cover 1028 is substantially reduced at and near the dispensing location 1035 in comparison to the other regions of the valve cover to thereby consistently direct the metered dosages through the one-way valve 1024 at the dispensing location throughout usage of the dispenser. The tapered and pointed configuration 1031 of the valve cover 1026 also reduces the surface area of the valve cover at the dispensing location 1035 to facilitate releasing substantially the entire metered dosage and substantially preventing the formation of dosage residue and thereby, in turn, providing a substantially consistent dosage volume and dispensing location on the dispensing tip throughout usage of the dispenser. If desired, the valve seat 1026 may define a recessed end face 1033 as shown in FIG. 18, for example, to further reduce the surface area and thus the surface tension at the dispensing location 1035.

Figure 20:
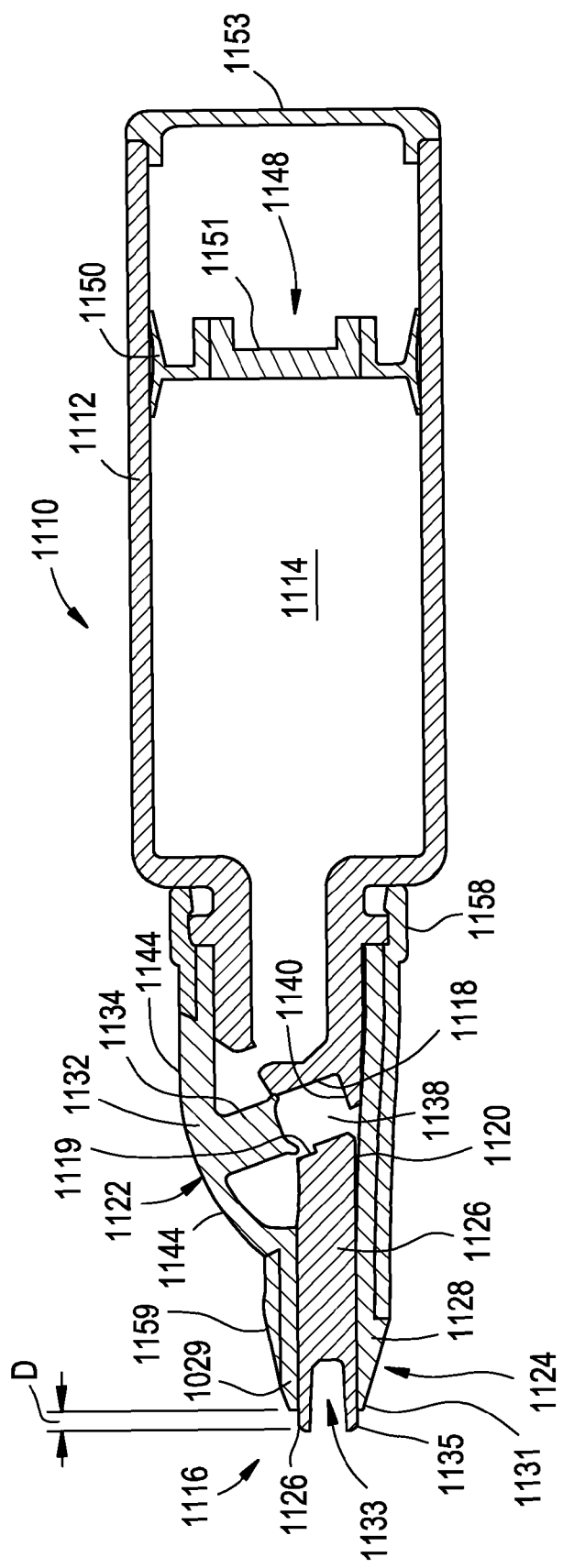
FIG. 20 is a cross-sectional view of a twelfth embodiment of a dispenser.

In FIG. 20, another dispenser embodying the present invention is indicated generally by the reference numeral 1110. The dispenser 1110 is substantially similar to the dispenser 1010 described above with reference to FIG. 19, and therefore like reference numerals preceded by the numeral "11" instead of the numeral "10" are used to indicate like elements. As with many of the dispensers described above, the dispenser 1010 is particularly suited for delivering substances to the eye, but alternatively may be used to deliver metered dosages to other target areas, such as the ear. The primary difference of the dispenser 1110 in comparison to the dispensers disclosed above is the configuration of the dispensing tip 1116. As can be seen, the end face 1133 of the valve seat 1126 extends axially outwardly a distance "D" relative to the valve cover 1128 at the dispensing location 1135. As with the dispenser of FIG. 19 described above, the valve cover 1128 is thicker in the region located diametrically opposite the dispensing location 1135 to prevent the passage of metered dosages through this region, and direct the dosages instead toward the dispensing location 1135. Similarly, on the diametrically opposite side of the valve cover 1128 (or the lower portion of the valve cover in the drawing), the valve cover 1128 tapers radially inwardly toward the axially-outermost point or dispensing location 1135 such that it is progressively thinner than the diametrically opposite portion of the valve cover. The securing member 1158 includes an axial extension 1159 that overlies the thicker regions of the valve cover 1128, but not the tapered region leading into and located at the dispensing location 1135. The securing member 1158, and in particular, the axial extension 1159 thereof, engages the outer surface of the valve cover 1128 to thereby substantially prevent the valve cover from expanding radially outwardly. If desired, the securing member 1158, and/or the axial extension 1159 thereof, may form an interference fit with the valve cover to further prevent such radial expansion of the valve cover. As a result, the hoop stress in the valve cover 1128 is substantially reduced in the tapered region at and near the dispensing location 1135 in comparison to the other regions of the valve cover to thereby consistently direct the metered dosages through the one-way valve 1124 at the dispensing location 1135 throughout usage of the dispenser.

In a currently preferred embodiment of the present invention for ophthalmic applications, the distance "D" to which the valve seat 1126 extends axially outwardly of the valve cover 1128, and the shape of the valve seat in this region, are selected based on the physical characteristics of the liquid dispensed, to achieve release of each metered dosage in a substantially single drop of substantially predetermined volume. If desired, the type of material employed for the valve seat 1126 or the tip portion thereof also may be selected to influence this goal (including, for example, the degree to which the material or its surfaces are hydrophobic or hydrophilic, or the coefficient of friction of such surfaces). In one such embodiment, the predetermined volume of each metered drop is within the range of about 15 to about 30 microliters, and most preferably within the range of about 18 to about 25 microliters. In one such embodiment, the predetermined volume is at least about 20 microliters. Accordingly, the distance "D" and shape of the release surface 1135 (and thus the surface area that contacts each metered dose) is selected to create sufficient surface tension for the predetermined substance being dispensed to create thereon a substantially single drop of substantially predetermined volume, yet not so much surface tension as to prevent release of the drop of predetermined volume therefrom. The tapered and pointed configuration 1131 of the valve cover 1126 also reduces the surface area of the valve cover at the dispensing location 1135 to facilitate releasing substantially the entire metered dosage and substantially preventing the formation of dosage residue, and thereby in turn providing a substantially consistent dosage volume and dispensing location on the dispensing tip throughout usage of the dispenser.

The bore 1118 defines one or more slots 1119 formed in the side wall thereof at the inlet to the bore to thereby define the volume of the compression zone 1138 located below the slots within the bore, and thus the volume of each metered dosage dispensed. The slots 1119 also facilitate the return of the actuator and piston assembly 1122 to its rest position as shown in FIG. 20 by reducing the back pressure on the piston when located nearest its rest position and in the region in which the spring force of the dome spring is lowest.

Figure 21:
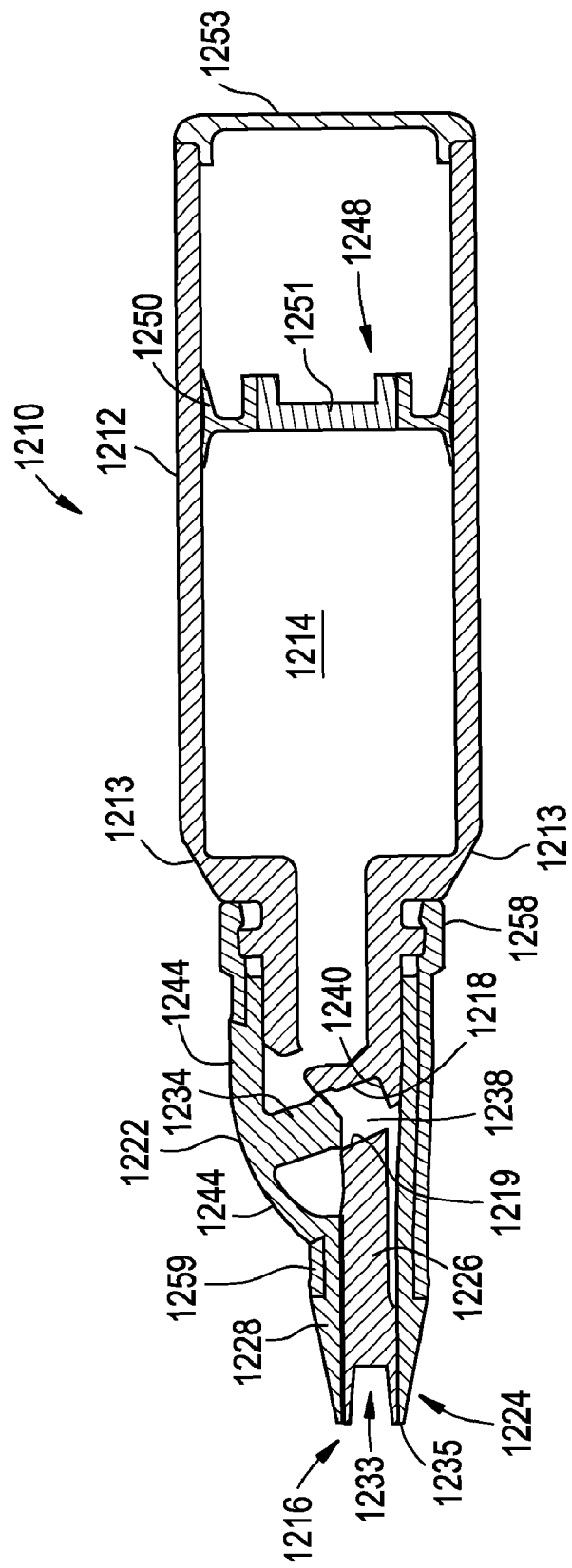
FIG. 21 is a cross-sectional view of a thirteenth embodiment of a dispenser.
Figure 22:
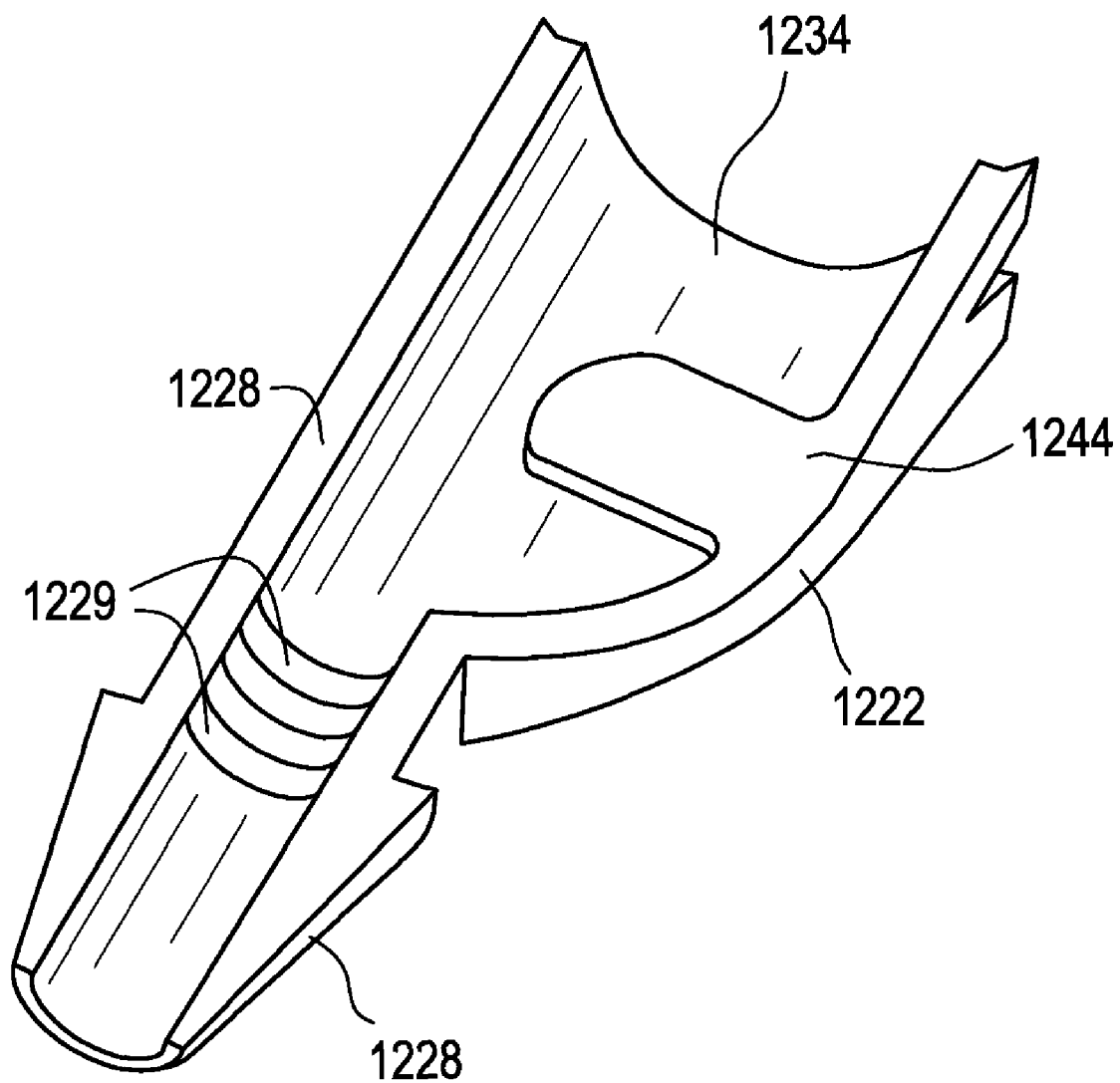
FIG. 22 is a partial, perspective view of the valve cover of the dispenser of FIG. 21.
Figure 23:
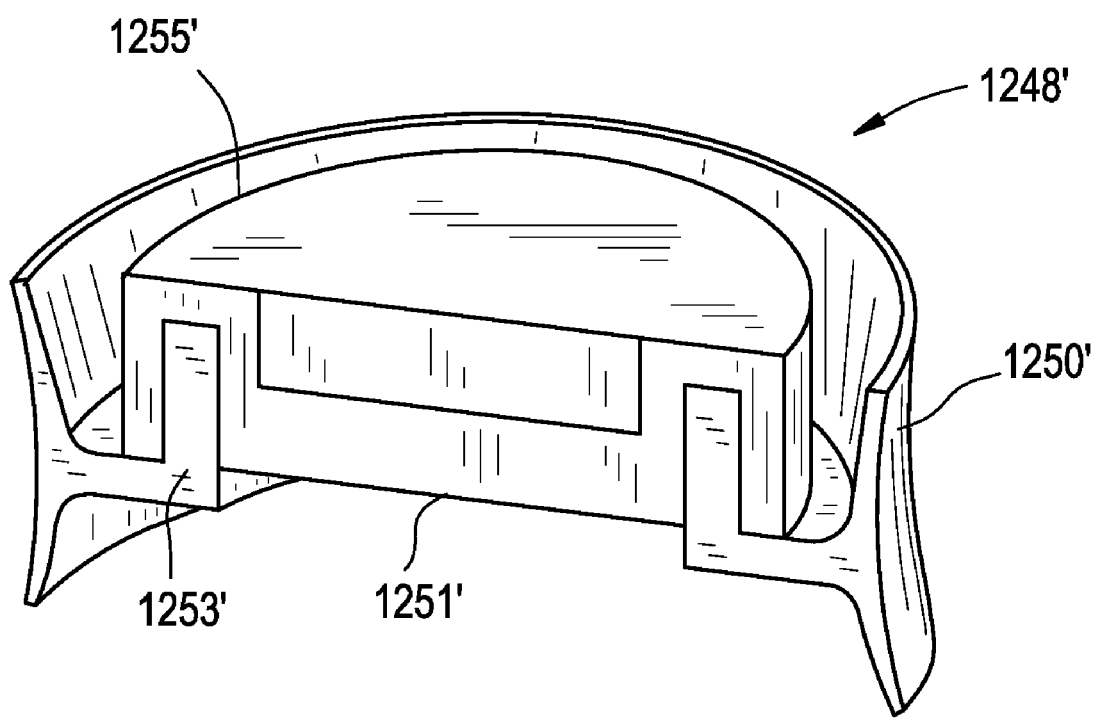
FIG. 23 is a partial, perspective view of an alternative embodiment of the plunger of the dispenser of FIG. 21.

In FIGS. 21 through 23 another dispenser embodying the present invention is indicated generally by the reference numeral 1210. The dispenser 1210 is substantially similar to the dispenser 1110 described above with reference to FIG. 20, and therefore like reference numerals preceded by the numeral "12" instead of the numeral "11" are used to indicate like elements. As with many of the dispensers described above, the dispenser 1210 is particularly suited for delivering substances to the eye, but alternatively may be used to deliver metered dosages to other target areas, such as the ear. The primary difference of the dispenser 1210 in comparison to the dispenser 1110 described above, is that the dispenser 1210 defines a substantially symmetrical valve cover 1228 at the dispensing tip. In addition, as shown in FIG. 22, the valve cover 1228 defines on its inner surface at the interface between the valve cover and valve seat a plurality of raised surface areas 1229 that are axially spaced relative to each other and corresponding recessed surface areas located between the raised surface areas. The raised surface areas 1229 project radially inwardly to a greater extent than do the corresponding recessed surface areas and the other inner surfaces of the valve cover, and thus form a greater degree of interference between the valve cover and valve seat in comparison to the other surfaces of the valve cover. In the illustrated embodiment, the raised surface areas 1229 define approximately twice the level of interference between such surface areas and the valve seat in comparison to the other inner surfaces of the valve cover. However, as may be recognized by those of ordinary skill in the pertinent art based on the teachings herein, this differential degree of interference may be changed as desired or otherwise required by a particular application, and may be, for example, within the range of about 1.5 to 2.5 times greater than the interference of adjacent valve cover surfaces. As can be seen, the raised surface areas 1229 are not annular, but rather extend through only a portion of the annular interface between the valve cover and the valve seat. In the illustrated embodiment, the raised surface areas extend throughout approximately 270° of the annular interface between the valve cover and valve seat, and preferably extend throughout a portion of the interface within the range of about 250° to about 290° of the annular interface. However, as may be recognized by those of ordinary skill in the pertinent art based on the teachings herein, these numbers may be changed as desired or otherwise required by a particular application.

One advantage of the raised surface areas is that they enhance the seal between the valve cover and valve seat without over-compressing the valve (i.e., without creating too high a valve-opening pressure). In addition, if the interference between the valve cover and valve seat is too high, the valve cover may bulge or otherwise become distorted in certain areas. Accordingly, the raised surface areas allow the interference between the valve cover and valve seat to be reduced in comparison to what otherwise might be required to maintain the integrity of the valve seal throughout shelf-life and usage of the dispenser, and thus may allow for a corresponding decrease in the valve-opening pressure. In addition, the raised surface areas facilitate in directing the valve flow through the angular extent of the interface that does not include the raised surface areas (i.e., the 90° portion located between the opposing ends of the raised surface areas). As can be seen, the angular extent between the ends of the raised surface areas is aligned with the dispensing location 1235 to facilitate directing the metered dosages thereto.

As shown in FIG. 21, the bore 1218 defines at its inlet an expanded annular portion or ring 1219 rather than the slots described above to thereby define the volume of the compression zone 1238 located below the annular ring 1219 within the bore, and thus the volume of each metered dosage dispensed. As with the slots described above, the annular ring 1219 facilitates the return of the actuator and piston assembly 1222 to its rest position as shown in FIG. 21 by reducing the back pressure on the piston when located nearest its rest position and in the region in which the spring force of the dome spring is lowest. As also shown in FIG. 21, the piston 1234 defines an approximately conically-pointed tip facing the stop surface 1240 of the bore to facilitate the action of the piston within the bore. As also shown typically in FIG. 21, the body 1212 may define a plurality of recessed surface areas or keys 1213, with corresponding raised surface areas located therebetween (not shown) to facilitate engaging the body in an assembly fixture as needed to align the body with the valve cover and/or for securing the components prior to and/or during assembly thereof.

Turning to FIG. 23, the dispensers may include a modified plunger 1248', particular for use in connection with applications employing a needle penetrable and laser re-sealable stopper 1251' as described above. In the illustrated embodiment, the needle penetrable and laser re-sealable stopper is over-molded to an axially-extending flange 1253' of the sealing member 1250'. As can be seen, the re-sealable stopper 1251' defines an axially-exposed face 1255' that is directed towards the back end of the body 1212. The face 1255' is adapted to engage a fixture (not shown) for securing the position of the plunger 1248' during needle filling through the stopper 1251'. In one such embodiment, the fixture engages the face 1255' and includes vacuum ports coupled in fluid communication with the face to secure the face to the fixture, and thereby secure the plunger to the fixture during needle penetration and filling through the stopper. As may be recognized by those of ordinary skill in the pertinent art based on the teachings herein, the shape and/or other physical features of the stopper and/or other aspects of the plunger may be changed as desired or otherwise required to allow the plunger to engage a needle filling fixture and thereby secure the position of the plunger during needle penetration and filling therethrough.

As may be recognized by those of ordinary skill in the pertinent art based on the teachings herein, numerous changes and modifications may be made to the above-described and other embodiments of the present invention without departing from the spirit of the invention as defined in the claims. For example, the components of the dispensers may be made of any of numerous different materials that are currently known, or that later become known for performing the function(s) of each such component. Similarly, the components of the dispensers may take any of numerous different shapes and/or configurations. Also, the dispensers may be used to dispense any of numerous different types of fluids or other substances for any of numerous different applications, including, for example, cosmetic, dermatological, ophthalmic or other pharmaceutical, cosmeceutical and/or OTC applications. In addition, the characteristics of the dispensers may be adjusted, including for example the shape and/or configuration of the dispensing tip, the volume of the metered dosages, and/or the valve opening pressure, to meet the requirements of any of numerous different applications and/or products to be dispensed, including without limitation products that are delivered topically, such as to the skin or to mucous membranes, products that are delivered to the ear (i.e., otic delivery), to the penis, nasally, vaginally, anally or orally. Further, the filling machines used to fill the dispensers of the present invention may take any of numerous different configurations that are currently known, or that later become known for filling the dispensers. For example, the filling machines may have any of numerous different mechanisms for sterilizing, feeding, evacuating and/or filling the dispensers. If desired, the surface contour of the valve seat may be adjusted to facilitate directing the valve-flow through a predetermined dispensing location at the valve tip. For example, the annular surface of the valve seat may define different angular segments, wherein the different angular segments are defined by different radii. In one such embodiment, the lower valve seat radii are provided in those areas where it is desired to achieve a higher stress concentration between the valve cover and valve seat, and thereby prevent or otherwise reduce the valve flow therethrough. The higher valve seat radii, on the other hand, are provided in those where it is desired to achieve a lower stress concentration between the valve cover and valve seat, and thereby enhance or otherwise increase the proportion of valve flow therethrough. In one such embodiment, the largest radius is aligned with the dispensing location, and the lowest radii are located on opposite sides of such location relative to each other. In addition, rather than use the needle penetrable and resealable actuator, plunger, or other like stopper, the dispenser may employ a filling valve as disclosed in the following patent application that is assigned to the Assignee of the present invention, and is hereby incorporated by reference as part of the present disclosure: U.S. application Ser. No. 10/843,902, filed May 12, 2004, titled "Dispenser and Apparatus and Method for Filling a Dispenser". In such alternative embodiments, the filling valve may extend through the body or otherwise may be coupled in fluid communication with the storage chamber to evacuate and/or fill the storage chamber. Alternatively, the dispenser may include one valve for evacuating the interior of the dispenser and another valve for filling the storage chamber of the dispenser. Still further, the piston and/or dispensing valve each may take a configuration that is different than that disclosed herein. Accordingly, this detailed description of currently preferred embodiments is to be taken in an illustrative, as opposed to a limiting sense.

What is claimed is:

1. A dispenser for dispensing a substance, comprising:
a body including a variable-volume storage chamber for storing the substance;
a dispensing portion connected with the body and including a compression chamber coupled in fluid communication with the storage chamber for receiving substance therefrom, and an outlet aperture coupled in fluid communication with the compression chamber;
a manually-engageable actuator mounted on the dispensing portion and including a manually engageable surface on an external side of the actuator and a compression surface on an internal side of the actuator, wherein the manually engageable surface is manually depressible between first and second positions to actuate the dispenser, and is normally biased in the direction from the second position toward the first position;
wherein the manually engageable actuator is defined by a flexible material, wherein an external side the flexible material defines the manually engageable surface and an underside of the flexible material defines the compression chamber; and
a one-way valve forming an external portion of the dispenser including a valve seat and a flexible valve cover seated on the valve seat and defining a normally-closed seam therebetween forming a fluid-tight seal between the valve cover and valve seat, wherein the flexible valve cover is movable relative to the valve seat and the seam is connectable in fluid communication with the outlet aperture to allow the passage of substance through the seam and out of the dispenser;
wherein (i) during movement of the manually engageable surface in the direction from the second position toward the first position, the variable-volume storage chamber is in fluid communication with the compression chamber for permitting substance to flow from the variable-volume storage chamber into the compression chamber, and (ii) during movement of the manually engageable surface in the direction from the first position toward the second position (a) the compression chamber is not in fluid communication with the variable-volume storage chamber and (b) the substance within the compression chamber is pressurized above the one-way valve opening pressure and dispensed through the normally closed seam of the one-way valve and out of the dispenser.

2. A dispenser as defined in claim 1, wherein the compression chamber is located axially with respect to the one-way valve and the actuator is located radially with respect to the one-way valve.

3. A dispenser as defined in claim 1, wherein the actuator is approximately dome shaped.

4. A dispenser as defined in claim 1, further comprising an approximately annular securing member coupled to the body and fixedly securing the valve cover thereto.

5. A dispenser as defined in claim 1, wherein the flexible valve cover is responsive to a flow of substance in the outlet aperture exceeding a valve opening pressure to move between (i) a normally-closed closed condition, and (ii) an open condition wherein portions of the valve cover axially spaced relative to each other substantially sequentially move substantially radially relative to the valve seat to allow the passage of substance through the seam and out of the dispenser.

6. A dispenser as defined in claim 1, wherein the compression surface is defined by one of (i) a piston located on the interior side of the actuator, and (ii) an interior wall of the actuator.

7. A dispenser as defined in claim 1, wherein the actuator includes a spring that biases the actuator in the direction from the second position toward the first position.

8. A dispenser as defined in claim 7, wherein the spring is formed integral with the actuator.

9. A dispenser as defined in claim 8, wherein the actuator is formed of an elastic material and the spring is defined by a wall of the elastic actuator.

10. A dispenser as defined in claim 1, wherein the dispenser is adapted for dispensing a substance that is at least one of a cosmetic and a pharmaceutical, and the dispensing portion includes an applicator surface defining a contour substantially conforming to a facial contour for facilitating application of the substance thereto.

11. A dispenser as defined in claim 1, wherein at least one of an axial end portion of the valve cover and valve seat defines a substantially pointed portion for facilitating release of substance therefrom.

12. A dispenser as defined in claim 11, wherein the pointed portion is defined by the valve cover and extends one of (i) radially inwardly, and (ii) radially outwardly.

13. A dispenser as defined in claim 11, wherein:
an axial end portion of the valve seat extends axially outwardly over the valve cover; and
the axial end portion of the valve seat defines at least one of a shape, surface area, coefficient of friction, and water absorption characteristic that is selected based on a predetermined product to be dispensed to create thereon a substantially single drop of substantially predetermined volume of the predetermined product thereon upon actuating the manually-engageable actuator, and to release said substantially predetermined volume in a substantially single drop therefrom.

14. A dispenser as defined in claim 1, wherein at least one of (i) the valve cover and valve seat define a differential degree of interference therebetween in between an upstream end toward a downstream end of the seam, (ii) the valve cover defines a decreasing cross-sectional thickness in a direction from an upstream end toward a downstream end of the seam, (iii) the valve seat defines an outer diameter that increases in a direction from an upstream end toward a downstream end of the seam, and (iv) the valve cover and valve seat define a configuration such that the energy required to move respective segments in the valve cover progressively decreases in a direction from an upstream end toward a downstream end of the seam.

15. A dispenser as defined in claim 14, wherein the valve cover defines a decreasing cross-sectional thickness in a direction from an upstream end toward a downstream end of the seam.

16. A dispenser as defined in claim 1, wherein the variable-volume storage chamber is defined by a flexible member.

17. A dispenser as defined in claim 1, further comprising a lobe projecting adjacent to the compression chamber that prevents fluid communication between the compression chamber and the variably volume storage chamber during movement of the manually engageable surface in the direction from the first position toward the second position.

18. A dispenser for dispensing a substance, comprising:
first means for forming a variable-volume chamber for storing the substance;
second means coupled in fluid communication with the first means for dispensing metered dosages of substance, and including third means for receiving a portion of the substance stored in the first means;
fourth means forming an external portion of the dispenser coupled in fluid communication with the second means (i) for normally sealing the second means along a seam and preventing the dispensing of substance below a threshold pressure through the second means, and (ii) for substantially sequentially opening the seam in an axial direction thereof to allow the passage of substance at a pressure greater than the threshold pressure through the second means and out of the dispenser;
fifth means that is manually engageable and radially depressible between first and second positions relative to an elongated axis of the dispenser for pressurizing the substance in the third means, wherein the third means is connectible in fluid communication between the first means and the fourth means, and (i) during movement of the fifth means in the direction from the second position toward the first position, the first means is in fluid communication with the third means for permitting substance to flow from the first means into the third means, and (ii) during movement of the fifth means in the direction from the first position toward the second position, the third means is not in fluid communication with the first means and a portion of the fifth means extends into the third means for pressurizing substance within the third means above an opening pressure of the fourth means and, in turn, dispensing the substance through the fourth means and out of the dispenser.

19. A dispenser as defined in claim 18, wherein the first means is a body portion of the dispenser; the second means is a dispensing portion defining a portion of the third means, the third means is a compression chamber coupled in fluid communication between the first means and the fourth means; the fourth means is a one-way valve including an axially-extending valve seat and an axially-extending flexible valve cover seated on the valve seat and defining a normally-closed, axially-extending seam therebetween forming a fluid-tight seal between the valve cover and valve seat; and the fifth means is a manually engageable, flexible actuator defining an underside that is receivable within the third means.

20. A dispenser as defined in claim 18, wherein the fifth means is located axially with respect to the fourth means and radially with respect to the third means, is elastically movable between the first and second positions, and is normally biased in the direction from the second position toward the first position.

21. A dispenser as defined in claim 18, wherein the fifth means is defined by a flexible material, wherein an external side the flexible material defines a manually engageable surface and an underside of the flexible material defines the third means.

22. A dispenser as defined in claim 1, wherein the valve seat and the valve cover are axially-extending and define an axially-extending seam.

23. A dispenser as defined in claim 1, wherein the manually-engageable actuator is depressible radially relative to an elongated axis of the dispenser.

* * * * *

UNITED STATES PATENT AND TRADEMARK OFFICE
CERTIFICATE OF CORRECTION

PATENT NO. : 8,007,193 B2  
APPLICATION NO. : 12/710516  
DATED : August 30, 2011  
INVENTOR(S) : Daniel Py et al.

Page 1 of 1

It is certified that error appears in the above-identified patent and that said Letters Patent is hereby corrected as shown below:

Claim 1, column 26, line 24 "external side the flexible" should be changed to --external side of the flexible--

Signed and Sealed this
Eighth Day of November, 2011

David J. Kappos
*Director of the United States Patent and Trademark Office*